US006121495A

United States Patent [19]
Babb et al.

[11] Patent Number: 6,121,495
[45] Date of Patent: Sep. 19, 2000

[54] ETHYNYL SUBSTITUTED AROMATIC COMPOUNDS, SYNTHESIS, POLYMERS AND USES THEREOF

[75] Inventors: David A. Babb, Lake Jackson; Dennis W. Smith, Jr., Fresno, both of Tex.; Steven J. Martin; James P. Godschalx, both of Midland, Mich.

[73] Assignee: The Dow Chemical Company, Midland, Mich.

[21] Appl. No.: 08/712,777

[22] Filed: Sep. 12, 1996

Related U.S. Application Data

[60] Provisional application No. 60/003,629, Sep. 12, 1995.

[51] Int. Cl.[7] .......................... C07F 9/50; C07C 321/00; C07C 22/02
[52] U.S. Cl. ............................... 568/17; 568/28; 568/38; 568/58; 568/332; 568/634; 568/659; 568/663; 568/716; 570/128; 570/182; 570/183
[58] Field of Search .................. 570/128, 182, 570/183; 568/58, 332, 635, 14, 8, 16, 17, 38, 28, 56, 634, 659, 663, 716; 585/25

[56] References Cited

U.S. PATENT DOCUMENTS

| | | | |
|---|---|---|---|
| 4,465,833 | 8/1984 | Lau et al. | 544/246 |
| 4,814,472 | 3/1989 | Lau | 556/431 |
| 5,169,929 | 12/1992 | Tour et al. | 528/397 |
| 5,227,457 | 7/1993 | Marrocco, III et al. | 528/183 |
| 5,236,686 | 8/1993 | Tour et al. | 423/445 |
| 5,264,511 | 11/1993 | Walton | 526/285 |
| 5,312,994 | 5/1994 | Bryant et al. | 568/306 |
| 5,334,668 | 8/1994 | Tour et al. | 525/416 |
| 5,338,457 | 8/1994 | Capozzola et al. | 210/652 |

FOREIGN PATENT DOCUMENTS 4024647 of 0000 Germany .

OTHER PUBLICATIONS

CA:121:178928 abs of J Org chem by Semmelhack 59(17) pp. 5038–5047, 1994.
CA:108:56180 abs of Angew Chem by Blanco 99(12) pp. 1276–1277, 1987.
CA: 113:172286 abs of J Chem Soc, Chem Comm by Field (13) pp. 931–933, 1990.
CA: 112:208376 abs of Angew Chem 102 (2) pp. 200–202, 1990.
S. Antoun et al., Preparation and Electrical Conductivity of Poly(1,4–Naphthalene Vinylene), *Journal of Polymer Science, Part C: Polymer Letters*; vol. 24, pp. 503–509 (1986).
Jens A. John et al., Synthesis of Polyphenylenes and Polynaphthalenes by Thermolysis of Enediynes and Dialkynylbenzenes, *Journal of American Chemical Society*; vol. 116, pp. 5011–5012 (1994).
G. Lehmann, Ladder–Like Conjugated Polymers, *Synthetic Metals*; vol. 41–43, pp. 1615–1618 (1991).
*Journal of the American Chemical Society*; vol. 94, No. 2; pp. 660–661 (1972).
Rainer Diercks et al., *Angw. Chem, Int. Engl.* vol. 25 No. 3; p. 266 (1986).
Robert H. Grubbs et al., Highly Unsaturated Oligomeric Hydrocarbons, *Chem. Ber.*, vol. 126: pp. 149–157 (1993).
James M. Tour, Soluble Oligo–and Polyphenylenes, *Advanced Materials*; vol. 6, No. 3; pp. 190–198 (1994).
Eric B. Stephens et al., Metal–Catalyzed Alkyneylation of (Bromophenyl)–Ologophenylene, *Advanced Materials* vol. 4, No. 9; pp. 570–572 (1992).
Eric B. Stephens et al., Metal–Catalyzed Alkyneylation of Brominated Polyphenylenes, *Macromolecues* vol.; 26, pp. 2420–2427 (1993).
Qing–Yun Chen et al., Palladium–Catalyzed Reaction of Phenyl Fluoroalkanesulfonates with Alkynes and Alkenes, *Tetrahedron Letters*, vol. 27, No. 10; pp. 1171–1174 (1986).
Jens A. John et al. Synthesis of Polyphenyls and Polynaphthalenes by Thermolysis of Enediyenes and Dialkynylbenzenes, *Journal of American Chemical Society*, vol. 116, pp. 5011–5012 (1994).
Teddy M. Keller, High Temperature Copolymer from Inorganic–Organic Hybrid Polymer and Multi–Ethynylbenzene; pp. 32–33.
Ann E. Mera et al. A Comparison of Acetylene–Containing Monomers Derived from Naphthalene; pp. 621–622.
K. M. Jones et al. Aromatic Acetylenes for Carbon Matrix Composite Materials; *Polymer Matter Science Engineering*, pp. 97–98.
Ann E. Mera, Resins Containing Naphthalene and Anthracene Units, *Poly Prepr. American Chemical Society, Div. Polymer Chemistry*; 1992, vol. 33, No. 2; pp. 345–346.
Jens A. John et al. Synthesis of Polyphenylenes and Polynaphthalenes by Thermolysis of Enediynes and Dialkynylbenzenes, *Journal of American Chemical Society*, vol. 116, No. 11; pp. 5011–5012 (1994).

*Primary Examiner*—Gary Geist
*Assistant Examiner*—Jean F Vollano

[57] ABSTRACT

Compounds of ethynyl aromatic compounds form polymers which have high thermal stability. The monomers are useful for coating a wide variety of substances such as dielectric coatings where high thermal resistance is desirable including electronic components such as computer chips.

16 Claims, No Drawings

ETHYNYL SUBSTITUTED AROMATIC COMPOUNDS, SYNTHESIS, POLYMERS AND USES THEREOF

This application claims benefit of provisional application 60/003,629, filed Sep. 12, 1995.

The present invention relates to ethynyl-substituted aromatic compounds, to polymers of ethynyl-substituted aromatic compounds, and to methods for the preparation and use of the ethynyl-substituted aromatic compounds and polymers thereof.

Polymeric materials which are relatively easy to process and are resistant to temperatures of 300° C. to 450° C. are of interest for preparing laminates, films, coatings, fibers, electronic components and composites. Depending on the specific end-use application, the polymers should exhibit one or more of the following properties: mechanical integrity, low moisture absorption, thermo-oxidative stability, thermal stability, solvent resistance, hydrolytic stability, resistance to highly acidic or basic solutions, a low coefficient of thermal expansion and a low dielectric constant. For example, in electronics, the material should exhibit a balance of low dielectric constant, good thermal stability and solvent resistance, and a low moisture uptake and coefficient of thermal expansion. In addition, processability can also be important to achieve uniform and defect-free films.

Polyimide resins are one class of materials which are commonly employed for preparing high strength films, fibers, composites, and coatings, including insulative or protective coatings in the electronics industry. However, polyimide resins tend to absorb water and hydrolyze, which can lead to corrosion and migration of metal ions. In addition, polyimides typically exhibit poor planarization and gap fill properties. Non-fluorinated polyimides exhibit undesirably high dielectric constants.

Polyarylenes are thermally stable polymers, but are often difficult to process due to low solubility in common organic solvents. A number of different routes for the preparation of high molecular weight polyphenylenes soluble in an organic solvent have been proposed. For example, U.S. Pat. No. 5,227,457, teaches introducing solubilizing groups such as phenyls onto the polymer chain. Unfortunately, these substituents may also make the resultant polymers sensitive to processing solvents. In another approach, cross-linkable polyphenylene compositions are prepared having a relatively low molecular weight initially, but which cross-link upon heating to form polymers exhibiting solvent resistance. (See, for example, U.S. Pat. Nos. 5,334,668; 5,236,686; 5,169,929; and 5,338,823). However, these compositions may not flow sufficiently to fill gaps, particularly submicron gaps, and planarize surfaces, a critical limitation in many applications, including electronics. Processable polyphenylenes have also been prepared by the reaction of a diacetylene with a biscyclopentadienone. However, the resulting polymers are thermoplastic materials and sensitive to organic solvents used in their processing.

Other polymers which are useful in electronic applications include poly(naphthalenevinylene) containing alternating naphthalene vinylene linkages; (see, for example, Antoun, S.; Gagnon, D. K.; Darasz, F. E.; Lenz, R. W.; *J. Polym. Sci. Part C: Polym. Lett.* 1986, 24, 503); poly (perylene) or poly(perinaphthalene) or substituted poly (perylene) or poly(perinaphthalene) (see, for example, Lehmann, G., *Synthetic Metals* 1991, 41–43, 1615–1618; and monoaryl ortho-diacetylenes such as phenyl-1,2-bis (phenylacetylene) and their reaction to form linear polynaphthalene (see, for example, John, Jéns A. and Tour, James M. in *J. Amer. Chem. Soc.*, 1994, (116) 5011–5012. However, these polymers are soluble in organic solvents and thermoplastics material.

In view of the deficiencies in the prior art, it is desirable to provide a compound having the desirable balance of physical and processing properties.

Accordingly, in one aspect, the present invention is an ethynyl aromatic compound of the formula:

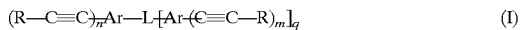

wherein each Ar is an aromatic group or inertly-susbtituted aromatic group; each R is independently hydrogen, an alkyl, aryl or inertly-substituted alkyl or aryl group; L is a covalent bond or a group which links one Ar to at least one other Ar; n and m are integers of at least 2; and q is an integer of at least 1. As such, the ethynyl aromatic compounds of the present invention have four or more ethynyl groups (for example, tetraethynyl aromatic compounds) and are useful as monomers in the preparation of polymers, including their oligomeric precursors.

In another aspect, the present invention is a polymer, including copolymers, which comprise units of:

wherein Ar' is the residual of the reaction of product of $(C{\equiv}C)_{\overline{n}}Ar$ or $Ar{-}(C{\equiv}C)_m$ moieties and R and L are as defined above.

In a particularly preferred embodiment, the copolymers of the present invention comprise units of:

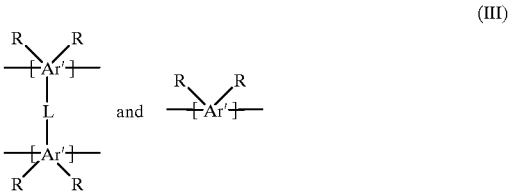

wherein Ar' and R are as hereinbefore defined.

The ethynyl aromatic compounds of the present invention, prior to substantial curing, for example, oligomers or oligomeric precursors of the final polymers, exhibit good solution and melt processability. The resulting thermoset polymers are generally resistant to the high temperatures and solvents commonly used in their processing. In addition, when cross-linked, the polymers exhibit an exceptional balance of solvent resistance and mechanical strength, without loss of electrical properties such as low dielectric constant and dissipation factor. Coatings of the polymer on a variety of substrates can be prepared using conventional techniques such as applying an oligomer of the monomers from solution and thereafter forming the polymer. The polymers can resist high temperatures such as the temperatures required to anneal aluminum which may be as high as 450° C. for cumulative times reaching 2 hours or more. In addition, the polymers can be prepared without volatile materials being formed during polymerization, and at relatively low polymerization and cross-linking temperatures.

Because of their high dielectric strength, resistance to degradation by heat, oxygen and moisture and many chemicals, the polymers of the present invention are particularly useful as capacitor dielectric (films); in displays such as flat panel displays, especially liquid crystal (LC) displays; and as integrated circuit (IC) encapsulates.

As such, the polymers are useful for applications such as laminates, coatings or thin films in making integrated circuits such as microprocessors, memory and multichip modules, as well as composite structures such as carbon matrices, as high performance matrix resins useful in aerospace and aircraft industries, high temperature adhesives and composite matrices, precursors for fibers or carbon glasses. In another aspect, the present invention is a substrate coated with the described polymer, for example, a computer chip having a coating of the described polymers such as a computer chip having the polymer as an interlayer dielectric insulation coating.

In yet another aspect, the present invention is a laminate having at least two layers at least one layer of which comprises a polymer of the present invention. Laminates of these polymers are particularly useful in electronics, building materials, matrix resins for aircraft and aerospace applications, and for applications requiring heat or weather resistance.

The invention is also a method for making the monomers of Formula (I). The method comprises:

(a) selectively halogenating a polyphenol to halogenate each phenolic ring with a halogen on one of the two available positions ortho to the phenolic —OH group;

(b) converting the phenolic —OH on the resulting poly(ortho-halophenol) to a leaving group which is reactive with terminal ethynyl groups, for example, sulfonate ester; and (c) reacting the product of step (b) with an ethynyl-containing compound or an ethynyl synthon in the presence of an aryl ethynylation catalyst and an acid acceptor to replace the halogen and the leaving group (for example, trifluoromethylsulfonate) with an ethynyl-containing group.

Those ethynyl-containing groups which are substituted with protecting groups (such as trimethylsilyl or 2-hydroxy-2-propyl) can optionally then be treated to remove the protecting groups to provide monomers of the present invention. Alternatively, the protecting groups can remain during polymerization.

In yet another aspect, the present invention is a compound of the following formula:

$$(RO_2SO)X_{(n-1)}-Ar-L+Ar(OSO_2R)X_{(m-1)}]_q \qquad (IV)$$

wherein X is a halo, preferably bromo, iodo, or chloro, more preferably bromo; m, n, and q are as hereinbefore defined, and R is any group such that $RSO_2O$ is a leaving group, preferably perfluoroalkyl.

The compounds of the present invention are ethynyl aromatic monomers of the formula:

$$(R-C\equiv C)_n Ar-L+Ar+(C\equiv C-R)_m]_q \qquad (I)$$

wherein each Ar, L, R, n, m and q are as hereinbefore defined. By the term "inertly-substituted", it is meant a group or moiety has one or more substituent groups which are essentially inert (that is, will either not react or, if reactive, will not significantly and deleteriously affect the properties of the compound or polymer made therefrom), and preferably inert, to the subsequent polymerization of the compound as well as any reagents or solvents used in subsequent processing. For example, the Ar group may be inertly-substituted with an alkyl such as an alkyl having from 1 to 12 carbon atoms; a halogen such as fluorine or chlorine; an alkene or conjugated alkene; phosphorus; silicon; sulfur; nitrogen; or oxygen and combinations thereof.

Similarly, each R group may be substituted with a halogen such as fluorine, chlorine and bromine; phosphorus; silicon; sulfur; nitrogen; —$CF_3$, —$OCH_3$, —$OCF_3$, or —O—Ph. Substitution with fluorine is especially preferred for achieving a low dielectric constant in the resulting polymers. In the formation of polymers resistant to high temperatures, it is usually preferable to avoid hydrogen atoms in a benzylic or allylic position or Ar groups or aromatic R groups substituted with straight-chain or branchedalkyls, esters or ethers.

The size of Ar and R are not particularly critical to the invention; however, the size of the Ar and R group, particularly the size of the R group, may, due to steric hindrance, undesirably interfere with subsequent polymerization of the compound, and Ar and R are selected accordingly. In general, any R group which does not prevent the formation of an aromatic ring from the reaction of the ethynyl groups on thermal treatment can be used. In general, each Ar will have from 6 to 50, preferably from 6 to 40, more preferably from 6 to 30, carbon atoms and each R, when aromatic will have from 1 to 20, more preferably from 6 to 15, most preferably from 6 to 10, carbon atoms.

Representative examples of Ar—(C≡C—R)—when R is aromatic include:

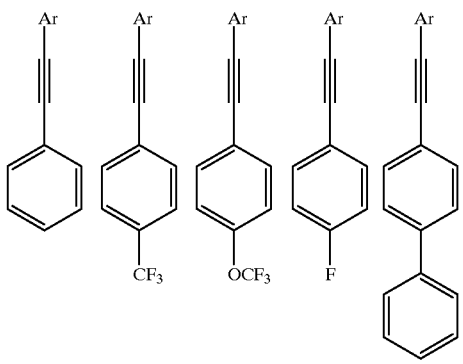

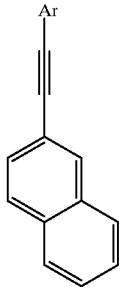

and representative L—Ar—(C≡C—R)$_m$ groups being

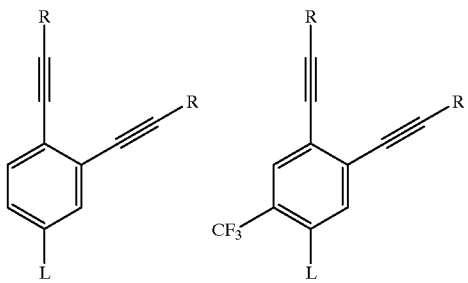

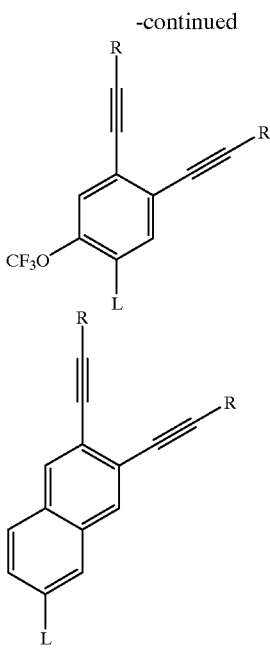

with Ar and aromatic R groups preferably being phenyl, phenylene, naphthyl, naphthylene, biphenyl, biphenylene, 2,2-diphenyl-1,1,1,3,3,3-hexafluoropropane, 9,9-diphenylfluorene, diphenylsulfide, diphenylether, trifluoromethylphenyl, trifluoro-methoxyphenyl, anthracene, phenanthrene, anthraquinone, triphenyl phosphine, triphenyl phosphine oxide groups, or aromatic silicon-containing groups.

In addition to being aromatic, R may also be hydrogen or an alkyl or inertly-substituted alkyl or cycloalkyl group. When greater reactivity is desired, R is preferably hydrogen or an alkyl group having from 1 to 8 carbon atoms. Preferably, R is unsubstituted or inertly-substituted phenyl, most preferably phenyl substituted with one or more fluorine atoms or a fluoroalkyl group having from 1 to 6 carbon atoms.

While L can be a covalent bond or any group linking Ar groups; L is preferably a bond, an unsubstituted hydrocarbon group, or inertly-substituted hydrocarbon group such as a hydrocarbon substituted with halogens (for example perfluoroalkyl); silicon or substituted silyl; oxygen, sulfur; nitrogen or substituted amine; phosphorous or substituted phosphine. The L group can also be a polymeric chain such as polyarylene or polyaryl ether (for example, polyphenylene, polynapthalene or polyphenylene oxide) of essentially any molecular weight, depending on the desired properties of the ethynyl substituted aromatic polymer. The preferred L is dependent on the desired properties of the resulting polymer with, in general, L preferably being a bond, oxygen, or an unsubstituted or inertly-substituted alkyl group having from 1 to 12, more preferably from 3 to 6, carbon atoms (for example, hexafluoropropane, or 9,9-fluorene)

Representative examples of compounds of the structure of Formula (I) include:

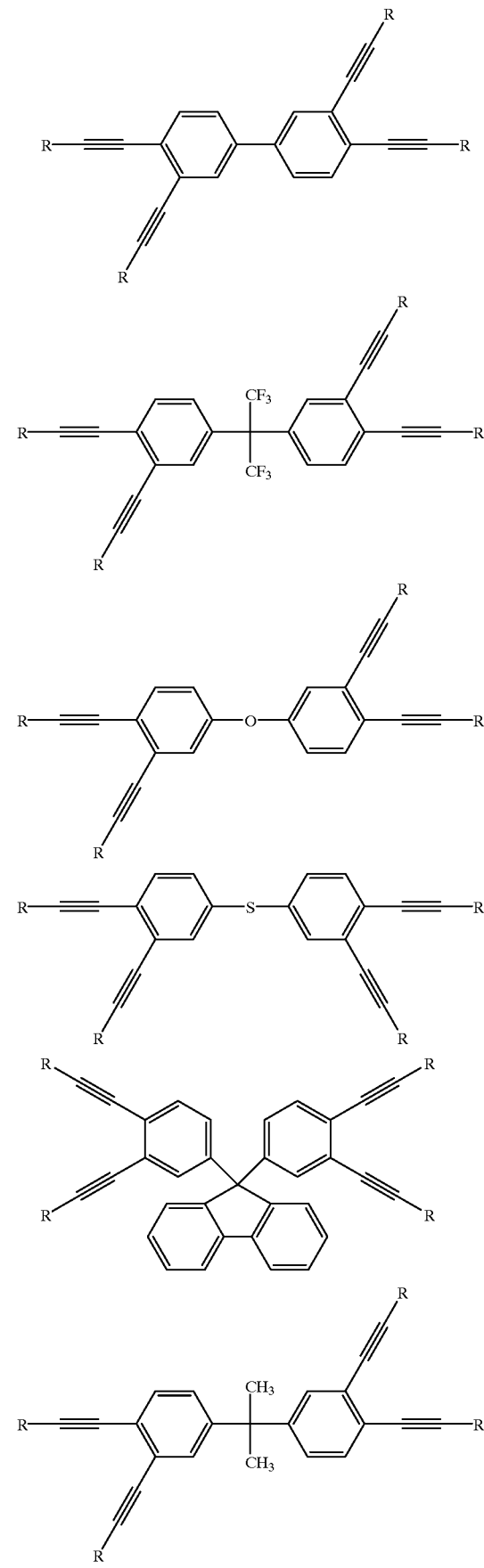

-continued

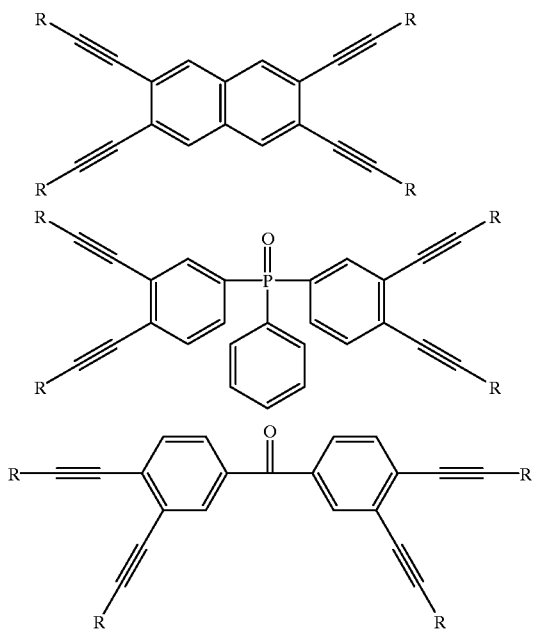

with Ar—L—Ar preferably being biphenyl such as biphenyl; 2,2-diphenyl propane; 9,9'-diphenyl fluorene; 2,2-diphenyl hexafluoro propane; diphenyl sulfide; oxydiphenylene; diphenyl ether; bis(phenylene)diphenylsilane; bis(phenylene) phosphine oxide; bis(phenylene)benzene; bis(phenylene)naphthalene; bis(phenylene)anthracene; thiodiphenylene; 1,1,1-triphenyleneethane; 1,3,5-triphenylenebenzene; 1,3,5-(2-phenylene-2-propyl) benzene; 1,1,1-triphenylenemethane; 1,1,2,2-tetraphenylene-1,2-diphenylethane; bis(1,1-diphenyleneethyl)benzene; 2,2'-diphenylene, 1,1,1,3,3,3-hexafluoropropane; 1,1-diphenylene-1-phenylethane; naphthalene; anthracene; or bis(phenylene)napthacene; more preferably biphenylene; naphthylene; p,p'(2,2-diphenylene propane) [—C$_6$H$_4$—C(CH$_3$)$_2$—C$_6$H$_4$—]; p,p'-(2,2-diphenylene-1,1,1,3,3,3 hexafluoropropane) and [—C$_6$H$_4$—C(CF$_3$)$_2$—C$_6$H$_4$—]. Most preferably, Ar—L—Ar is biphenyl; 2,2-diphenyl propane; 9,9'-diphenyl fluorene; 2,2-diphenyl hexafluoro propane; diphenyl sulfide; diphenyl ether; bis(phenylene)diphenylsilane; bis(phenylene) phosphine oxide; bis(phenylene)benzene; bis(phenylene)naphthalene; bis(phenylene)anthracene; or bis(phenylene)napthacene.

The ethynyl groups on each Ar are on adjacent carbon atoms within the ring. It is believed that they dimerize upon application of heat to form an aromatic ring having a 1,4-diradical which serves to polymerize and/or cross-link the compound. While not being bound by theory, it is believed that this dimerization occurs via Bergman cyclization such as disclosed by Warner et al. in *Science,* 268, Aug. 11, 1995, pp. 814–816.

The ethynyl aromatic monomers are preferably bis(o-diethynyl) monomers (herein also referred to as BODA (bis(ortho-diacetylene)monomers), which means there are at least two sets of adjacent ethynyl groups on the monomer, that is, at least one set of ethynyl groups on each Ar group. Preferably, the ethynyl aromatic compound contains from 2 to 4, most preferably 2 or 3, diethynyl sets, most preferably, except when additional cross-linking is desired, 2 sets (that is, four) of ethynyl groups.

The monomers of the present invention are advantageously prepared by:

(a) selectively halogenating, preferably in a solvent, a polyphenol (preferably a bisphenol) to selectively halogenate, preferably brominate, each phenolic ring with one halogen on one of the two positions ortho to the phenolic —OH group;

(b) converting the phenolic —OH on the resulting poly(ortho-halophenol), preferably in a solvent, to a leaving group such as a sulfonate ester (for example, a trifluoromethanesulfonate ester prepared from trifluoromethanesulfonyl halide or trifluoromethane sulfonic acid anhydride) which is reactive with and replaced by terminal ethynyl compounds; and (c) reacting the reaction product of step (b) with an ethynyl-containing compound or an ethynyl synthon in the presence of an aryl ethynylation, preferably palladium, catalyst and an acid acceptor to simultaneously replace the halogen and the trifluoromethylsulfonate with an ethynyl-containing group (for example, acetylene, phenylacetylene, substituted phenylacetylene or substituted acetylene.

In the halogenation step (a), the polyphenol corresponds to (HO)—Ar—L—Ar—(OH), wherein Ar and L are as hereinbefore described. Preferred polyphenols include 4,4'-biphenol; 9,9-bis(4'-hydroxyphenyl)fluorene; 4,4'-dihydroxydiphenyl ether; 4,4'-dihydroxydiphenyl thioether; 2,2-bis(4'-hydroxyphenyl)hexafluoropropane; bis(4'-hydroxyphenyl); phenyl phosphineoxide; trisphenols such as 1,1,1-tris(4'-hydroxyphenyl)ethane; 1,1,1-tris(4'-hydroxyphenyl) phosphinexoxide; 2,6-naphthalenediol; and 2,7-naphthalenediol.

The conditions at which the halogenation step (a) are conducted are not particularly critical, provided selective halogenation takes place and the conditions most advantageously employed will depend on a variety of factors including the specific polyphenol being halogenated and the halogenating agent. In general, the reaction is conducted in a solvent for the bisphenol and the halogenated product such as carbon tetrachloride or methylene chloride or a mixture of these solvents with glacial acetic acid. In the case where n and m in Formula (I) are each 2, the temperature, pressure (which is most commonly atmospheric) and stoichiometry of bromine are controlled such that only one bromine atom is attached ortho- to each phenol group. In general, temperatures of from −20° to 100° C., preferably from 0° to 50° C. are employed, with reaction times being from 1 to 168 hours.

The conditions at which the halogenated product is converted to a sulfonate ester are also not particularly critical, provided the desired conversion is achieved. Those conditions most advantageously employed depend on a variety of factors including the specific halogenated polyphenol and other reactants, with the temperature and pressure (generally atmospheric) being maintained to react the halopolyphenol with a sulfonate esterification reagent such as trifluoromethanesulfonyl halide, preferably trifluoromethanesulfonyl chloride or trifluoromethane sulfonic acid anhydride, to form the corresponding poly(2-halophenyl trifluoromethanesulfonate) aryl of the formula:

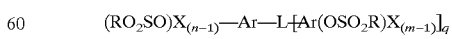

preferably of the formula:

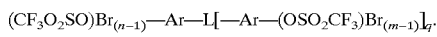

The reaction is advantageously conducted in a solvent such as methylene chloride, carbon tetrachloride, or chloroform at a reaction temperature of from −20° to 100° C., preferably from 0° to 50° C., for a reaction time of from 0.5 to 96 hours.

The final step (c) is conducted at a temperature and pressure (generally atmospheric) sufficient to react poly(2-halophenyl trifluoromethanesulfonate) with an ethynyl-containing compound or an ethynyl synthon in the presence of an aryl ethynylation, preferably palladium, catalyst and an acid acceptor. A solvent for the acid acceptor and the reactants and reaction product is advantageously employed and is generally a polar aprotic solvent. Representative solvents include tetrahydrofuran, dimethylforamide, dimethylacetamide, dimethylsulfoxide, triethylamine, diisopropylamine, other amine solvents and mixtures of amine solvents.

Ethynyl-containing compounds which can be employed include those compounds reactive with the poly(2-bromophenyl trifluoromethanesulfonate), and are preferably of the formula R—C≡C—X, where R is as previously defined and X is hydrogen or a copper (I) salt. These include phenylacetylene, pentafluorophenylacetylene, trifluoromethylphenylacetylene, and 4-fluorophenylacetylene.

Ethynyl synthons are compounds which form ethynyl groups in the final product and include such compounds as trimethylsilylacetylene. The ethynyl group is optionally protected by such groups as acetals, ketones, ketals, hydroxymethyl, tetrahydropyran protected hydroxy methyl, dimethylcarbinol, ethyl ester, trimethylsilane, especially trimethylsilyl and dimethylcarbinol.

Acid acceptors which can be employed include inorganic acid acceptors like potassium carbonate, amines such as triethylamine, triisopropylamine, piperidine, diisopropylamine, and pyridine, as well as mixtures of these amines and/or inorganic acid acceptors. Most preferably, the acid acceptor is triethylamine.

Aryl ethynylation catalysts which can be employed include copper and/or palladium, a phosphine source preferably triaryl phosphines (for example triphenyl phosphine, tri-o-tolyl phosphine), whether the palladium is in the form of metallic palladium or complexed palladium, either zero valent or precursors thereof (for example $Pd^{II}$ including, for instance, palladium diacetate and palladium dichloride). Preferred catalysts include palladium acetate and chloride with a phosphine source and copper, such as disclosed by Ritter, *Synthesis*, 1993, pp. 749–750; Grissom et al. *J. Org. Chem.* 1993, 58, 5422–5427 at p. 5423; Jones, et al., *Polymer*, 36(1), pp. 187–192; Chem et al., *Tet. Lett.*, 27(10) pp. 1171–1174 (1986); Alami et al., *Tet. Lett.*, 34(40) pp.6403–6406 (1993); Nguyen, et al. *Inorganica Chimics Acta* 220, pp. 289–296 (1984); and Cacchi et al. *Synthesis*, 1986, pp. 320–322.

In general, the ethynylation reaction is conducted at temperatures from 40° C. to 180° C., preferably from 60° C. to 100° C., more preferably from 70° C. to 95° C., for a reaction time from 1 to 48 hours, preferably from 1 to 24 hours, more preferably from 2 to 6, hours.

The concentrations at which the monomers are most advantageously employed in the organic liquid reaction medium, when employed, are dependent on a variety of factors including the specific monomers and organic liquid employed and the polymer being prepared. In general, the reactants are employed to prepare a solution containing from 1 to 70, preferably from 5 to 50 percent solids.

The preparation of bis(ortho-diacetylene)-6F, a most preferred monomer of the present invention, can be depicted as follows:

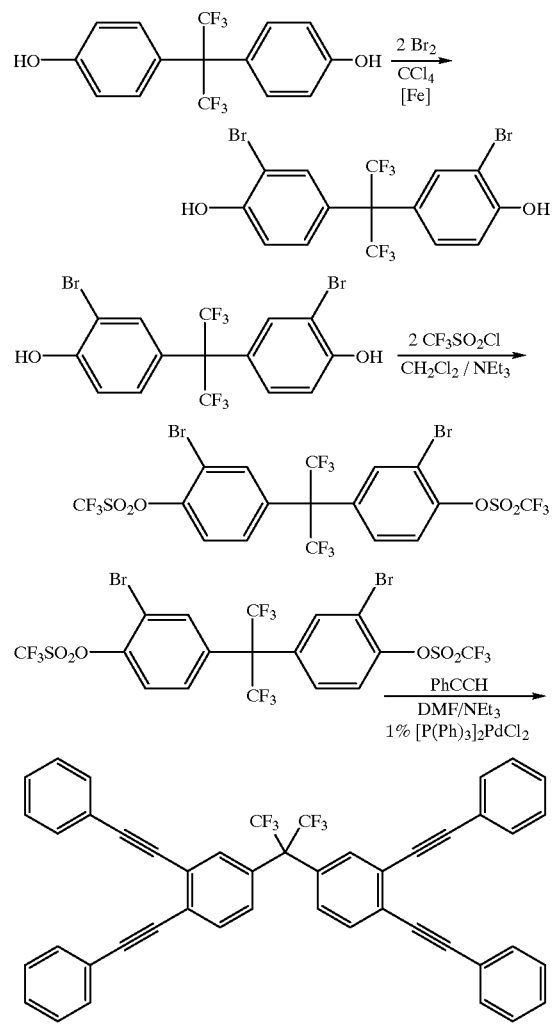

Following the preparation of the ethynyl aromatic compound (or monomer), the product can be recovered by conventional methods or, if prepared in a solvent, used directly without recovery.

The ethynyl aromatic monomers of Formula (I) are useful to prepare polymers of either Formula (II) or (III). While not being bound by theory, it is believed that the ethynyl groups, specifically those of ortho orientation, on the aromatic ring cyclize upon heating, forming a dehydro aromatic ring which reacts to form a polymer chain. Monomers with more than two ortho ethynyl groups (that is, more than one set of ethynyl groups) are used to form thermoset polymers and depending on the concentration of monomer having more than one set of ortho-ethynyl groups may contain from almost none (that is, a polymer having essentially repeat units of Formula (II) only) to substantial segments of linear polymer chain structure (that is, a polymer of Formula (III)).

The ethynyl aromatic monomers can be thermally polymerized. Polymerization can be detected by increasing viscosity or reaction exotherm. Polymerization will generally occur at a temperature more than 150° C., but polymerization temperatures are preferably at least 180° C., more preferably at least 210° C. The polymerization temperature preferably does not exceed that temperature which would result in undesirable degradation of the resulting polymer, which means polymerization is generally conducted at a temperature less than 300° C. for monomers having benzylic hydrogen atoms, and, for monomers not having a benzylic hydrogen, less than 450° C., preferably less than 400° C., more preferably less than 350° C. The polymerization temperature will vary with Ar—L—Ar and R, with smaller R groups like H generally requiring lower temperatures than larger R, and more conjugated Ar and R (when aromatic) groups requiring lower temperatures than less conjugated Ar and R groups. For instance, when R or Ar is anthracene, the polymerization is more advantageously conducted at a lower temperature than when Ar or R is phenyl.

While not being bound by theory, representative untits of Formula (II) are believed to have the following structural formulae:

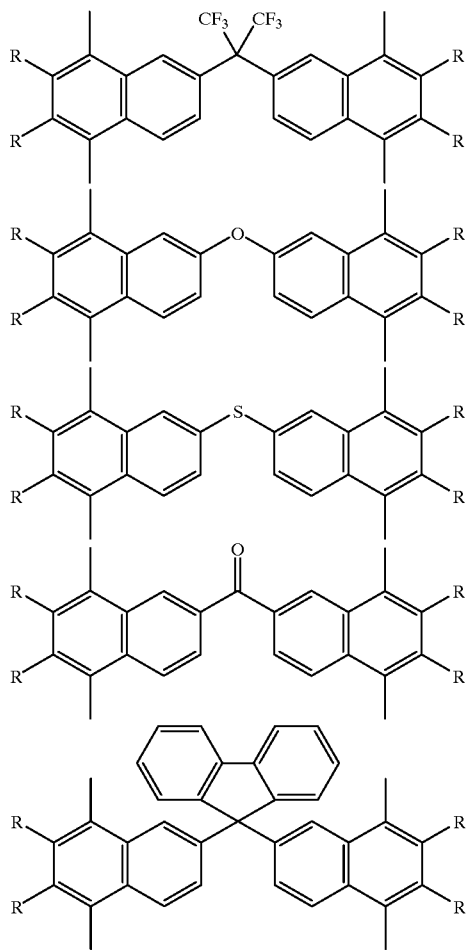

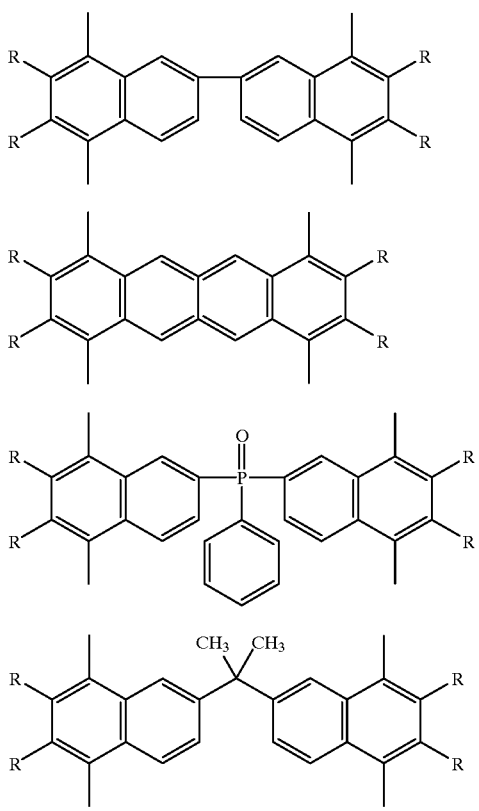

Polymerization is conveniently conducted at atmospheric pressure, but pressures higher or lower than atmospheric pressure can be employed.

The polymerization may be conducted in the presence of agents for controlling (accelerating) the cyclization reaction such as free radical initiators, or the chlorides disclosed by Warner et al. in Science 269, pp. 814–816 (1995) can be employed in the polymerization reaction.

While not being bound by theory, it is believed that polymerization of the most preferred bis(ortho-diacetylene)-6F can be depicted as follows:

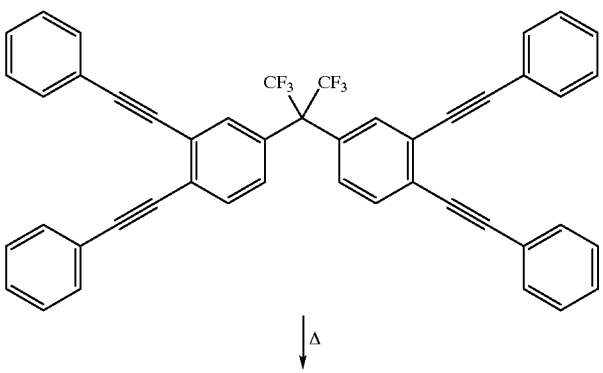

-continued

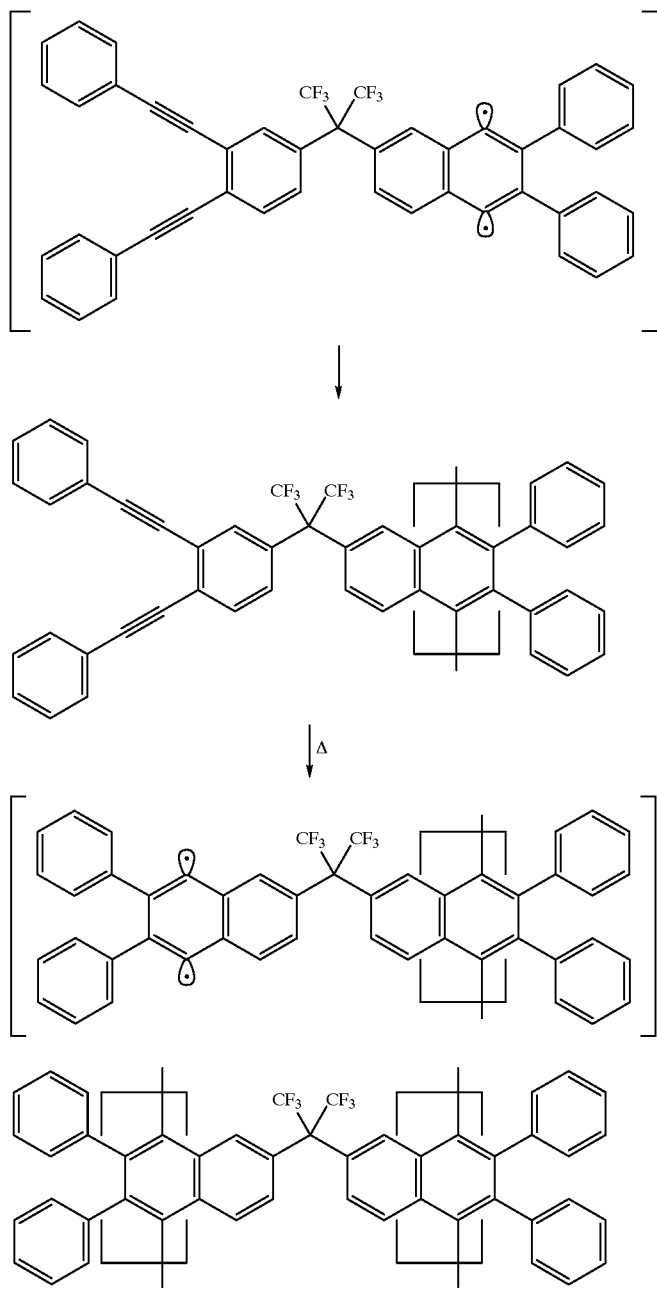

While the specific conditions of polymerization are dependent on a variety of factors including the specific ethynyl aromatic monomer(s) being polymerized and the desired properties of the resulting polymer, in general, the conditions of polymerization are dictated or determined by the specific end-use application of the polymer.

Polymerization may be conducted neat or in a solvent and whether a solvent is employed is dependent on the specific monomers employed, polymer formed, processing conditions and end-use application. For example, when the resulting polymer is to be used as powder-coating, or in resin transfer molding or injection molding, polymerization is often advantageously conducted neat or in bulk. Alternatively, a solvent can be employed in the polymerization. In general, a solvent is employed for applications where the polymer or an oligomeric precursor of the polymer is to be applied from solution, such as solution spin-coating. In such applications as well as others, the monomers are heated until oligomers (that is, a mixture of an unspecified amount of unreacted monomers in combination with the reaction products of monomers which have a molecular weight higher than the monomer but less than its gel point, generally a number average molecular weight of less than 100,000, often less than 25,000, more often less than 15,000 and an Mw/Mn ranging from 1 to 100, preferably from 1 to 50 and more preferably from 1 to 25, as determined by size exclusion chromatography using polystyrene calibration standard) are formed. Preferably, the oligomer solution is a liquid solution having a viscosity convenient for coating. In general, such a solution will comprise from 1 to 70, preferably from 10 to 60, weight percent solids. Subsequently, the oligomers are applied in or from solution and subsequently heated to remove solvent and to cure or cross-link the oligomers to the final thermoset polymer.

In general, the solvent most advantageously employed will be a solvent for both the monomer and the resulting oligomer such as diisopropylbenzene; 1,3,5-triisopropylbenzene; 1-methyl-2-pyrrolidinone; mesitylene; gama-butyrolactone; cyclohexanone; cyclopentanone; diphenylether; and 1,3-di-t-butylbenzene.

The time and temperature most advantageously employed in forming the oligomers will vary depending on the specific monomers employed, particularly their reactivity, the specific monomers and oligomers, and the organic liquid. In general, the oligomers are formed at temperatures of from 150° C. to 250° C. and for a time of from 1 to 48 hours, and the additional chain extension (advancement) and cross-linking conducted at a higher temperature of from 200° C. to 450° C., preferably from 225° C. to 400° C., and for a time of from 0.5 to 10 hours, more preferably from 0.5 to 2 hours. The chain extension and curing temperatures normally will cause evaporation of the solvent.

Depending on the desired properties of the polymerized product, two or more different ethynyl aromatic monomers having two or more pairs of ethynyl groups can be copolymerized, or one or more ethynyl aromatic monomer (s) having two or more pairs of ethynyl groups can be copolymerized with a monomer having only two (that is, one pair) polymerizable ethynyl groups to form polymers having linear segments. The comonomer employed will affect the toughness, glass transition temperature, adhesion, solution viscosity, processability and flexibility in the final polymer. When the compounds of the invention are copolymerized with monomers which can be used to prepare linear polynaphthalene polymers, the resulting thermoset copolymer will often exhibit improved mechanical properties such as increased toughness (as measured by K1c and G1c values according to ASTM methods numbered D5045).

The polymers and copolymers of the present invention are useful for applications such as coatings or thin films in making electronics and computer chips, especially in microprocessors, and also in memory chips and in EPROMS (erasable programmable read-only memory), as well as composite structures; high performance matrix resins useful in aerospace and aircraft industries; high temperature adhesives and composite matrices; ceramic precursors for fibers or carbon glasses useful in automotive, electronic, aerospace and medical implant industries; electro/optical polymers; conducting polymers; non-linear optics; photo-electro luminescence applications such as light-emitting diodes (LED); and thermochromic indicators, having semiconductor-like properties upon oxidation and/or reduction useful in LEDs. Matrix applications are similar to those explained in Hergenrother, *Encyclopedia Polymer Science and Engineering,* vol. 1, 2d ed. John Wiley & Sons, NY (1985) pp. 61–86.

The polymer or oligomeric precursor of the polymer can be applied by a number of methods such as vapor deposition (chemical or physical), sputtering, solution deposition, liquid-phase epitaxy, screen printing, melt-spinning, dip-coating, roll-coating, spinning, brushing (for example varnish), spray-coating, powder-coating, plasma-deposition, dispersion-spraying, solution-casting, vacuum-deposition, slurry-spraying, dry-powder-spraying, fluidized bed techniques, welding, explosion methods including the Wire Explosion Spraying Method and explosion bonding, press-bonding with heat; plasma polymerization; dispersion in a dispersion media with subsequent removal of dispersion media; pressure bonding; heat bonding with pressure; gaseous environment vulcanization; extruding molten polymer; hot-gas welding; baking-coating; and sintering. Mono- and multilayer films can also be deposited onto a substrate using a Langmuir-Blodgett technique at an air-water or other interface.

The oligomer can be directly cast as a film, applied as a coating, or poured into a non-solvent to precipitate the oligomer. Water, methanol, acetone and other similar polar liquids are typical non-solvents which can be used to precipitate the oligomer. If the oligomer is obtained in solid form, it may be further processed using conventional compression molding techniques or melt-spinning, casting or extrusion techniques provided the solid precursor has a sufficiently low glass transition temperature.

For example, the polymers can be used as powder coatings in the electronics industry for coatings of electronic components such as resistor networks, capacitors and hybrids and applied, for instance, by automatic fluidized beds, dipping equipment, and electrostatic spraying. When used as a powder coating, the polymer preferably has a fusing temperature below the melting point of tin-lead solder, more preferably below 150° C., most preferably below 130° C. Alternatively, monomers having a melting point below 200° C. can be applied as a powder and heated to effect polymerization. Other components of a desired coating can be optionally mixed with the monomers before polymerization such that the components remain in the final polymerized coating.

More commonly, the oligomers are processed directly from the organic liquid reaction solution. An organic solution of the oligomer can be cast or applied and the solvent evaporated and molecular weight increased (chain extension or advancement) to form the final polymer upon exposure to a sufficiently high temperature.

When applying the monomer, oligomeric prepolymer or polymer from solution, specific conditions of polymerization and other processing parameters most advantageously employed are dependent on a variety of factors, particularly the specific monomer, oligomer or polymer being deposited, the conditions of coating, the coating quality and thickness, and the end-use application, with the solvent being selected accordingly. Representative solvents which can be employed include hydrocarbons such as o-, m- or p-xylene, mesitylene, toluene, and triisopropylbenzenebenzene; chlorinated hydrocarbons such as chlorobenzene and dichloromethane; ketones such as methyl ethyl ketone, isopherone, acetone, methyl isobutyl ketone, cyclopentanone and cyclohexanone; esters such as isoamyl acetate, n-butyl acetate, ethyl acetate, cellosolve acetate, methyl cellosolve acetate and gamma-butyrolactone; ethers such as diglyme and, tetrahydrofuran; amides such as N,N-dimethylformamide; and other polar solvents such as nitromethane, or 1-methyl-2-pyrrolidinone.

Substrate(s) which can be coated can be any material which has sufficient integrity to be coated with the monomer, oligomer or polymer. Representative examples of substrates include wood, metal, ceramics, glass, other polymers, paper, paper board cloth, woven fibers, non-woven fiber mats, synthetic fibers, Kevlar™, carbon fibers, silicon and other inorganic substrates and their oxides. The substrates which are employed are selected based on the desired application. Preferred materials include glass, including glass fibers (woven, non-woven or strands); ceramics; metals such as aluminum, magnesium, titanium, copper, chromium, gold, silver, tungsten, stainless steel, Hastalloy™, carbon steel, other metal alloys and their oxides; and thermoset and thermoplastic polymers such as epoxy resins, polyimides, perfluorocyclobutane polymers, benzocyclobutane polymers, polystyrene, polyamides, polycarbonates, and polyesters.

The substrate may be of any shape, and the shape is dependent on the end-use application. For instance, the substrate may be in the form of a disk, plate, wire, tubes, board, sphere, rod, pipe, cylinder, brick, fiber, woven or non-woven fabric, yarn (including commingled yarns), ordered polymers, and woven or non-woven mat. In each case the substrate may be hollow or solid. In the case of hollow objects, the polymer layer(s) is on either or both the inside or outside of the substrate. The substrate may comprise a porous layer, such as graphite mat or fabric, glass mat or fabric, a scrim, and particulate material.

The polymers adhere directly to many materials such as compatible polymers, polymers having a common solvent, metals, particularly textured metals, silicon or silicon dioxide, especially etched silicon or silicon oxides, glass, silicon nitride, aluminum nitride, alumina, gallium arsenide, quartz,and ceramics. However, when increased adhesion is desired, a material may be introduced to improve adhesion.

Representative examples of such adhesion promoting materials are silanes, preferably organosilanes such as trimethoxyvinylsilane, triethoxyvinylsilane, hexamethyldisilazane $[(CH_3)_3-Si-NH-Si(CH_3)_3]$, or an aminosilane coupler such as γ-aminopropyltriethoxy silane, or a chelate such as aluminum monoethylacetoacetatediisopropylate $[((isoC_3H_7O)_2Al(OCOC_2H_5CHCOCH_3))]$. In a preferred method, a toluene solution of the chelate is spread on a substrate and then baked at 350° C. for 30 minutes in oxygen to form a very thin (for example 5 nanometer) adhesion promoting layer of aluminum oxide on the surface. Other means for depositing aluminum oxide are likewise suitable. Alternatively, the adhesion promoter, preferably in an amount of from 0.05 weight percent to 5 weight percent based on the weight of the monomer, can be blended with the monomer before polymerization, negating the need for formation of an additional layer.

Additional adhesion promoters useful in the practice of the invention include Chemloc™ speciality elastomer adhesives; fluoroepoxides; vinyl tri-tert-butyl silane peroxide; neoalkoxytitanates; neoalkoxyzirconates; iminoxyl radical compounds; polyarylene sulfide resins; aromatic polyethersulfone resins; aromatic polyether ketone resins; alkoxycontaining silicon compounds; organotitanates; organohydrogensilicon compounds; m-aminophenol (optionally in a blend with a phenoplast); chromic acid; phosphoric acid; polyalkylsilicate containing a finely divided metal such as zinc; chromium III complexes of compounds such as fumaric acids; curable epoxy resins; ammonium chromate; ammonium phosphate; chromium/chromium oxide mixtures; carboxyl-containing alpha-olefin polymers; fluorinated acids and alcohols; organic complexes of Group 2B or 8 metals; fluoropolymer particles; fluorinated rubber, optionally containing tackifiers such as urethane, epoxy or acrylic resins; hydrocarbon polymers with halogenating agents; triallyl cyanurate; triallyl isocyanurate; silicon tack agent; perfluoroalkoxy resin with resin containing imide linkages; polysulfidic silane compounds; epoxy adhesive; alkali and/or alkaline earth alumino-borosilicate glass; bischloroalkyl vinyl phosphonate; polyurethane mastic; polyester film bases; polyamide acid salt; metal oxides; fluorine resin promoters optionally containing oxidants and/or inorganic acids; methylmethacrylate copolymers; zinc phosphate; zinc dispersion, water-hardening cements; peroxy organic compounds; fluorine resin containing asbestos paper; lithium polysilicate; powdered acid and alkali-resistant inorganic substance (such as silica, graphite, molybdenum sulfate, or chromium oxide); aluminum borophosphate; alkyl silicates; alkali metal silicates; polyamine-imides; polyvinylcinnamic acid (optionally exposed to ultra-violet light), and deposited carbon layers.

Adhesion can also be enhanced by surface preparation such as texturizing (for example, scratching, etching, plasma treating, or buffing) or cleaning (for example, degreasing or sonic cleaning); otherwise treating (for example, plasma, solvent, $SO_3$, plasma glow discharge, corona discharge, sodium, wet etching, or ozone treatments) or sand blasting the substrate's surface or using electron beam techniques such as 6 MeV fluorine ions; electrons at intensities of 50 to 2000V; hydrogen cations at 0.2 to 500 ev to 1 MeV; helium cations at 200 KeV to 1 MeV; fluorine or chlorine ions at 0.5 MeV; neon at 280 KeV; oxygen enriched flame treatment; or an accelerated argon ion treatment.

Fillers including glass; copper oxide and other metal oxides; colloidal silica; glass fibers; water-hardening cements; mineral fibrils such as potassium titanate, titanium dioxide or boehmite fibrils;or boehmite in other forms, can also be used to improve adhesion. The fillers can optionally be coated or treated (for example with surfactant or adhesion promoter) to improve adhesion to the polymer. Processes involving grafting such monomers as acrylic esters and/or other vinyl compounds to the polymer (for example using catalysts or radiation), and optionally treating the grafted molecules (for example saponification), may also be used to increase adhesion to the polymer.

The polymer can be applied in combination with other additives to enhance performance. Representative of such additives are metal-containing compounds such as magnetic particles, for example, barium ferrite, iron oxide, optionally in a mixture with cobalt, or other metal containing particles for use in magnetic media, optical media, or other recording media; conductive particles such as metal or carbon for use as conductive sealants, conductive adhesives, conductive coatings, electromagnetic interference (EMI)/radio frequency interference (RFI) shieldingcoating, static dissipation, and electrical contacts. When using these additives, the polymer may act as a binder.

The polymers of the present invention are also useful in seals and gaskets, preferably as a layer of a seal or gasket, for example around a scrim, also alone. In addition, the polymer is useful in anti-fouling coatings on such objects as boat parts; electrical switch enclosures; bathtubs and shower coatings; in mildew resistant coatings; or to impart flame resistance, weather resistance, or moisture resistance to an article. Because of the range of temperature resistance of the polymers, the polymers may be coated on cryogenic containers, autoclaves, and ovens, as well as heat exchangers and other heated or cooled surfaces and on articles exposed to microwave radiation. The polymers may also be employed as protection against the environment (that is, protective against at least one substance or force in an object's environment, including conditions of manufacture, storage and use) such as coatings to impart surface passivation to metals, semiconductors, capacitors, inductors, conductors, solar cells, glass and glass fibers, quartz and quartz fibers.

The polymers are particularly useful in electronic packaging such as multichip modules, multi-layer chips, microwave circuits, planarization layers, optical interconnect lines, circuit boards, cable insulation and The polymers are also useful as environmentally protective layers and impact absorbing layers for micromachines. When doped, the polymers are useful as conducting layers for such applications as in LEDs and non-linear optics (NLOs).

In addition, the polymers of the present invention can be applied to gallium arsenide and its homologues, which are frequently used in semiconductor devices such as high-speed transistors, high speed integrated circuits, light-emitting diodes, and laser diodes; silicon dioxide, which is often formed on silicon (preferably surface-treated such as with silicon nitride or phosphorus doping to enhance adhesion) which is commonly used as an insulator in semiconductor devices; phosphorus-doped silicon dioxide; chromium, which is useful as an opaque layer in optical masks; copper and copper foil.

In such cases, the surface onto which a polymer film is applied is preferably clean and free from dust particles to avoid adhesion problems and/or defects in the film. Cleaning of a silicon wafer surface may, for instance, involve: (1) boiling in a solvent, for example trichloroethylene, for example, for 5 minutes, (2) washing in another solvent, for example acetone (room temperature), for a similar length of time followed by (3) boiling in an acid, for example concentrated nitric acid, for example, for 15 minutes. Other substrate treatments include, for instance, etching silicon dioxide, with aqueous hydrofluoric acid (HF); hexamethyl disilane (HMDS) treatment of polysilicon, silicon dioxide, phosphorus doped silicon dioxide or silicon nitride.

The ethynyl aromatic compound or oligomer thereof is applied to obtain a, preferably continuous and/or uniform coating, followed by an initial heating to remove solvents, for example at 100° to 200° C., and then by curing at 190° to 350° C. In a particularly preferred embodiment of this invention, one or more layers of the polymer are applied over optical fibers, for example glass fibers, typically by applying an oligomer solution, preferably of sufficient viscosity to spread evenly to form a uniform coating; removing the solvent to form a, preferably tackless, coated fiber by rapid heating, for example in a plasma (UV, electron beam) or infrared (IR) oven; optionally followed by additional heat-curing to achieve a polymer which is preferably at least 50, more preferably at least 80, most preferably at least 99, percent cured.

In fabrication of microelectronic devices, relatively thin defect-free films, generally from 1 to 200, preferably from 1 to 20, $\mu$m thickness, can be deposited on a supporting inorganic substrate (preferably clean) for example silicon; or silicon-containing materials such as silicon dioxide, alumina, copper, silicon nitride; aluminum nitride; aluminum, quartz, and gallium arsenide. Coatings are conveniently prepared from solutions of an oligomer having molecular weight, for instance, of 2,000 Mn, 15,000 Mw, 25,000 Mz (high average), in any of a variety of organic solvents such as xylene, mesitylene, and n-butyl acetate. The dissolved oligomer (or prepolymer) can be cast onto a substrate by common spinand spray-coating techniques. The viscosity of these solutions is important in controlling coating thickness by either deposition technique.

Layer(s) of polymers can be patterned such as for photoresists and by such means as wet-etching, plasma-etching, reactive-ion etching (RIE), dry-etching, or photo laser ablation, such as illustrated by *Polymers for Electronic Applications,* Lai, CRC Press (1989) pp. 42–47. Patterning can be accomplished by multilevel techniques in which the pattern is lithographically defined in a resistlayer coated on the polymeric dielectric layer and then etched into the bottom layer. A particularly useful technique involves masking the portions of polymer (or prepolymer) not to be removed, removing the unmasked portions of polymer, then curing remaining polymer, for example thermally.

The polymers of the present invention are particularly useful to planarize materials such as silicon wafers used in semiconductors to allow the production of smaller (higher density) circuitry. To achieve the desired planarity, a coating of the oligomer or polymeric precursor is applied from solution such as by spin-coating or spray-coating, to flow so as to level any roughness on the surface of the substrate. These methods are illustrated by such references as Jenekhe, S. A., *Polymer Processing to Thin Films for Microelectronic Applications* in Polymers for High Technology, Bowden et al. ed., American Chemical Society 1987, pp. 261–269.

When used for planarization, a solution, preferably of prepolymer, is spread onto the substrate, rotated at a constant rotating speed, which is advantageously held for a time sufficient to allow preceding to an even thickness, for example 30 to 60 seconds. The resulting solution film, thinned by centrifugal force, is dried to form a solid film. In the case of silicon wafers, the polymers can effectively be applied and allowed to adhere during thermal cycling to reduce deviation in optical flatness often caused by oxide layer deposition.

After a polymer film is formed, for example by a spin-coating process, the film is conveniently baked. The baking evaporates solvent remaining in the film and generally polymerizes the monomer and/or oligomer more completely. Baking temperatures are preferably from 180° C. to 350° C., more preferably from 250° C. to 350° C. The polymer planarization layer can optionally be smoothed by polishing. A planarization layer is preferably from 0.1 $\mu$m to 5 $\mu$m thick, more preferably from 0.1 $\mu$m to 2 $\mu$m.

The polymers of the present invention are also useful in reinforced composites in which a resin matrix polymer is reinforced with one or more reinforcing materials such as a reinforcing fiber or mat. Representative reinforcing materials include fiber glass, particularly fiber glass mats (woven or non-woven); graphite, particularly graphite mat (woven or non-woven); Kevlar™; Nomex™; and glass spheres. The composites can be made from preforms, dipping mats in monomer or oligomer, and resin transfer molding (where the mat is placed into the mold and monomer or prepolymer is added and heated to polymerize). While the polymers are particularly useful as exterior layers, and dielectric layers, they are also useful as reinforcing or other interior layers, such as reinforcements in tires, and drive belts,.

The following examples are presented to illustrate the present invention and should not be construed to limit its scope. Ratios, parts, and percentages are by weight unless otherwise stated.

EXAMPLE 1

Preparation of 2,2-Bis(3',4'-di(phenylethynyl)-phenyl)-1,1,1,3,3,3-hexafluoropropane 2,2-((3,3'-Dibromo-4,4'-dihydroxy)phenyl)-1,1,1,3,3,3-hexafluoropropane To a 250 milliliter (mL) round-bottom flask (equipped with a gas vent attached to an acid gas scrubber) containing 150 mL of carbon tetrachloride ($CCl_4$) and 10 mL glacial acetic acid (HOAc) maintained at room temperature was added 16 grams (g) (0.048 moles) of 2,2-bis(4'-hydroxyphenyl)-1,1,1,3,3,3-hexafluoropropane with agitation. Iron powder (1.5 g) was added to the mixture and then 9.71 g of fuming liquid bromine (0.0972 mole) was added dropwise to the mixture over 6 hours. The resulting solution was heated to 35° C. With continuous agitation, the reaction mixture was maintained at 35° C. for 48 hours. At that time, the entire amount of bisphenol had been converted to 2-bis(3,3'-dibromo-4,4'-dihydroxypheny)-1,1,1,3,3,3-propane.

The reaction mixture was transferred to a separatory funnel where it was washed once with saturated aqueous sodium bicarbonate solution and twice with deionized water. The $CCl_4$ solution was then dried over anhydrous magnesium sulfate($MgSO_4$), filtered and the solvent was evaporated to provide 23.2 g of a yellow powder. This corresponds to 0.047 mole or a yield of 97.95 percent, 93.4 percent pure by GC analysis having the properties:

IR: (cm−1): 3506.7 (—OH), 1605.3, 1578.2, 1499.7 (Ar), 1256, 1208.9, 1175.3, 1136.7 (C—F), 1046 (C—O).

Mass spectrum, m/e (%): 423 (45.4), 424 (57.2), 425 (88.9), 426 (65.5), 427 (52.0), 428 (33.2), 492 (45.1), 494 (100.0), 496 (37.5)

This product was isolated and used for the next reaction without further purification.

2,2-Bis(3-bromo-4-trifluoromethanesulfonatophenyl)-1,1,1,-3,3,3-hexafluoropropane The dibrominated bisphenol (23.2 g, 0.047 mole) was dissolved in 150 mL of dichloromethane ($CH_2Cl_2$) and 15 mL (0.108 mole) of dry triethylamine. To this mixture, maintained at 8° C.–12° C. was added 18.2 g trifluoromethanesulfonyl chloride (0.108 mole) dissolved in 30 mL of $CH_2Cl_2$ over 30 minutes. While maintaining the solution at 8° C. to 10° C., the reaction mixture was agitated for two hours, then transferred to a separatory funnel and washed successively with two portions of aqueous 5 percent HCl solution (100 mL each), two portions of saturated aqueous sodium bicarbonate solution (75 mL each), then once with deionized water. The $CH_2Cl_2$ solution was then dried over anhydrous $MgSO_4$, filtered to remove the drying agent, and evaporated to provide 28.7 g of 2,2-bis(3-bromo-4-trifluoromethanesulfonatophenyl)-1,1,1,-3,3,3-hexafluoropropane as a light yellow solid (0.38 mole, 80.8 percent yield) having the following characteristics:

IR (cm−1): 1479.0, 882.5, 737.3 (Ar), 1429.3, (SO3), 1137.2, 1213.5 (C—F).

1H NMR (400 MHz, CDCl3): d 7.4 (4H, br, m), 7.74 (2H, s).

13C NMR (100 MHz, CDCl3): d 63.64 (hept, C(CF3)2, J=30 Hz), 116.57, 116.98, 122.97, 130.94, 133.71, 135.81, 147.83.

19F NMR (376 MHz, CDCl3): d −64.27 (6F, s), −73.86 (6F, s).

DEP/MS m/e (%): 758(5), 624(4), 207(5), 69(100).

2,2-Bis(3,4-di(phenylethynyl)phenyl)-1,1,1,3,3,3-hexafluoropropane

To a 250 mL Parr steel autoclave with glass insert equipped with mechanical stirrer, thermocouple and pressure gauge and maintained under a dry and inert atmosphere was added 10.0 g (0.013 mole) of 2,2-bis((3-bromo-4-trifluoromethanesulfonato)phenyl)-1,1,1,3,3,3-hexafluoropropane, followed, in order, by 1.85 g (2.64 millimole, 0.05 equivalent) of bis(triphenylphosphine) palladium (II) chloride, 0.40 g (2.11 millimole, 0.04 equivalent) of copper (I) iodide, 18.69 g (0.185 mole, 3.5 equivalent) of diisopropyl amine, 18.86 g (0.185 mole, 3.5 equivalent) of phenyl acetylene and finally 60 mL of tetrahydrofuran. The autoclave was sealed and purged with nitrogen for 5 minutes, then stirred for 1 hour at 26° C. At that time, a heating mantle was installed and the reactor heated at 65° C. to 70° C. for 20 hours and then at 105° C. for 13 hours with rapid and constant stirring.

Upon cooling to room temperature, the dark mixture was added to 100 mL of $CH_2Cl_2$ and 200 mL of distilled water. The aqueous layer was separated and washed three times with 75 mL of $CH_2Cl_2$. The organic layers are combined and washed three times with 100 mL saturated aqueous ammonium chloride then twice with distilled water, gravity filtered, dried over anhydrous $MgSO_4$, filtered and reduced to dryness by rotary evaporation. This crude product mixture was stirred in hot hexane and the insoluble portion was predominantly a mixture of phenylacetylene addition products along with other polyunsaturated oligomers. The hexane mixture was deposited on neutral alumina and was separated by column chromatography, first by eluting extensively with hexane, followed by elution with a mixture of six parts hexane and four parts $CH_2Cl_2$ to remove the product from the alumina. The solvent was removed and the product oil suspended in twice its volume of hexane. With gentle swirling, the product crystallizes and was washed with hexane to remove any entrained material. The isolated product was a light yellow crystalline solid with a melting point (m.p.) of 162° C. to 164° C. It was isolated in an unoptimized yield of 54 percent. It has the following characteristics:

$^1$H NMR (400 MHz, CDCl3): d 7.30–7.40 (13H, br, m), 7.52–7.62 (13H, br, m).

$^{13}$C NMR (100 MHz, CDCl3): d 64.0 (hept, C(CF3)2, J=30 Hz), 87.23, 87.48, 94.54, 95.38 (−CCPh) 122.77, 126.16, 126.93, 128.36, 128.40, 128.71, 128.78, 129.4, 131.63, 131.72, 132.51, 133.11.

$^{19}$F NMR (376 MHz, CDCl3): d −63.84 (s).

FTIR (cm$^{-1}$): 3059, 2998 (w ArH), 2216 (w, alkyne), 1599, 1495 (st), 1437, 1262 (br, st, CF), 1209 (br, st, CF), 1178 (br, st), 1100 (sh), 963, 827, 756, 691 cm−1.

DEP/MS m/z (%): 704 (100), all other fragments<5%.

EXAMPLE 2

Preparation of 3,3',4,4'-Tetra(phenylethynyl) biphenyl 3,3'-Dibromo-4,4'-dihydroxybiphenyl (Method 1)

Into a 3-L, 5-necked Morton type flask equipped with a mechanical stirrer, a thermocouple in a glass thermocouple well, and a dropping addition funnel was placed 200.83 g 4,4'-biphenol (1.07 mole), 2.5 liters of $CH_2Cl_2$, 40 mL of HOAc, and 1.37 g of iron powder (0.0245 mole). The reaction mixture was cooled to 10° C., and 370.86 g of liquid bromine (2.32 moles) was added over two days. The temperature in the flask varies from 10° C. to 18° C. over the course of the reaction.

The crude reaction mixture was filtered to remove solids, and the filtrate was placed on a rotary evaporator to evaporate the $CH_2Cl_2$. The residue was washed with saturated aqueous sodium bicarbonate, then with deionized water. The solid residue was dried on a rotary evaporator, then added to 1 liter of $CCl_4$ and heated to 60° C. to dissolve the solids. The resulting solution was cooled and the product of the reaction was collected as a crystalline solid. The solid product was washed with two portions of 250 mL of hot hexane to remove colored by-products, yielding 230 g of 3,3'-dibromo-4,4'-dihydroxybiphenyl as a white crystalline solid (81 percent pure, 61.5 percent yield). The main by-products from the reaction were roughly an equal mixture of mono-brominated and tri-brominated biphenols.

3,3'-Dibromo-4,4'-dihydroxybiphenyl (Method 2)

In an alternative method, 20.0 g of 4,4'-biphenol (0.1075 mole) was added to a 4:1 mixture of $CCl_4$/HOAc and 36 g of bromine was added dropwise over 3 hours. The mixture was allowed to stir for 72 hours and the reaction was found to be 89 percent complete with the remainder being unreacted starting material. The mixture was washed twice with deionized water, causing an emulsion layer that separated slowly. The remaining $CCl_4$ layer was removed by evaporation and the residue was dissolved in warm $CH_2Cl_2$. The insoluble portion was filtered and the $CH_2Cl_2$ was washed with deionized water. The solution was dried over anhydrous $MgSO_4$, filtered and evaporated to provide 28.6 g of 3,3'-dibromo-4,4'-dihydroxybiphenyl (0.083 mole, 77.2 percent yield) as a light pink solid, with an m.p. of 118° C. to 121° C. and having the following characteristics:

FTIR ($cm^{-1}$): 676.6 (0.19), 733.8 (0.20), 809.4 (0.054), 823.0 (0.61), 865.7 (0.27), 964.9 (0.12), 1040.4 (0.50), 1061.0 (0.16), 1137.0 (0.50), 1206.5 (0.91), 1245.3 (0.53), 1275.3 (0.87), 1341.1 (0.65), 1370.4 (0.47), 1427.7 (1.00), 1490.2 (0.82), 1571.4 (0.18), 1603.5 (0.27), 3315.6 (0.056).

Mass Spec, m/e (%): 53 (20.4), 62 (15.6), 63 (18.4), 74 (20.5), 75 (16.6), 77 (12.8), 124 (12.4), 125 (16.5), 126 (24.7), 152 (12.2), 153 (18.0), 154 (17.3), 155 (46.9), 156 (14.1), 342 (9.14), 343 (14.9), 344 (100), 345 (15.6), 346 (47.7), 347 (6.1).

3,3'-Dibromo-4,4'-ditrifluoromethanesulfonato) biphenyl (Method 1)

A 2-L, 5-necked Morton type flask fitted with a mechanical stirrer, thermocouple well, dropping addition funnel and nitrogen pad was dried at 150° C. for 4 hours with a nitrogen sweep. To the reactor was added 229 g (0.67 mole) of 3,3'-dibromo-4,4'-dihydroxybiphenyl and 1 liter of $CH_2Cl_2$. The solution was cooled to 10° C. 138 G (1.37 mole) of triethylamine was slowly added to the cooled mixture to maintain the reaction mixture at a temperature between 10° C. and 15° C. Trifluoromethanesulfonic acid anhydride (378.0 g, 1.34 mole) was then added dropwise from a dropping addition funnel over 2 hours and 10 minutes. During this addition, the temperature of the reaction mixture varied from 5° C. to 14° C. After the addition, the reaction mixture was raised to 22° C. for 16 hours to complete the reaction. The crude mixture was then washed with 500 mL of water followed by 500 mL of saturated sodium bicarbonate and then again by 500 mL of deionized water. The $CH_2Cl_2$ was evaporated and the residue was dissolved in hot hexane saturated with acetonitrile. The solution was cooled and the separated acetonitrile phase contained the black impurities of the product mixture. The hexane phase was isolated, heated to 60° C. and cooled to crystallize the desired product. The product was thus isolated (110 g, 95.5 percent pure, 33 percent yield) as a white crystalline solid with an m.p. of 69° C. to 70.5° C. It was suggested that the low yield of this preparation may be due to substantial solubility of 3,3'-dibromo-4,4'-di (trifluoromethanesulfonato)biphenyl in the wash water and certainly in the acetonitrile phase used to collect the impurities.

3,3'-Dibromobiphenyl-4,4'-ditriflate (Method 2)

In a second procedure, 28.56 g of 3,3'-dibromo-4,4'-biphenol (0.083 mole) was dissolved/suspended in 160 mL of $CH_2Cl_2$ in a 1-L, 5-necked flask. Upon the addition of 25 mL of triethylamine the solution briefly cleared, then set into a thick paste. The dibromobiphenol solution was cooled to 10° C. with constant stirring and 28 g of trifluoromethanesulfonyl chloride (0.166 mole) dissolved in 40 mL of $CH_2Cl_2$ was added dropwise over 30 minutes. The thick solution became less viscous, but the solids did not completely dissolve. After complete addition, the solution was warmed to 22° C. and agitated overnight. The crude reaction mixture was washed twice with 5 percent HCl (100 mL each), saturated aqueous $NaHCO_3$ (75 mL), and deionized water (100 mL). The deionized water wash caused an emulsion that broke slowly. The $CH_2Cl_2$ solution was separated and dried over anhydrous $MgSO_4$, then filtered and evaporated to provide 42 g of the trifluoromethanesulfonate ester (0.069 mole) as a light brown solid. The yield was 83.2 percent and the product was 95 percent pure with the following characteristics:

FTIR ($cm^{-1}$): 723.4 (0.12), 747.0 (0.17), 839 (0.23) 886.0 (0.50), 1036.4 (0.23), 1135.4 (0.58), 1180.0), 0.38), 1206.4 (1.00), 1248.8 (0.37), 1433.1 (0.88), 1469.0 (0.38).

Mass Spec, m/e (%): 69 (22.3), 126 (44.6), 127 (10.4), 381 (8.0), 383 (17.3), 385 (7.8), 473 (39.3), 473 (39.3), 474 (23.0), 475 (100), 476 (22.7), 477 (47.3), 478 (10.0), 606 (5.6), 608 (10.6), 610 (5.5).

3,3',4,4'-Tetra(phenylethynyl)biphenyl

Oven-dried 3,3'-dibromo-4,4'-di (trifluoromethanesulfonato)biphenyl (60.85 g, 0.10 mole) was added to a 1-L, 5-necked flask with DMF (270 mL) and triethylamine (270 mL). The solution was purged continuously with nitrogen. After sweeping the reactor contents with nitrogen for 20 minutes, dichlorobis (triphenylphosphine) palladium II catalyst was added and the reaction mixture was heated to 60° C. 16.5 G of phenylacetylene was then added as a sho, causing an exotherm that increased the temperature to 80° C. The mixture was cooled to 70° C. and the temperature was maintained at 70° to 80° C., while an additional 33.5 g of phenylacetylene was added dropwise. The reaction temperature was then held at 75° C. for 3 hours.

Analysis of the crude reaction mixture by LC at this point indicated a significant amount of unreacted starting material and products of intermediate conversion. An additional 10 g of phenylacetylene and 1 g of catalyst were added and the reaction mixture was heated at 85° C. for one hour. At this time, the LC indicated conversion was complete. The cooled reaction mixture was diluted with 500 mL of $CH_2Cl_2$ and washed with three 1-L portions of 10 percent HCl. The $CH_2Cl_2$ solution was isolated and evaporated to provide a crude solid product which was suspended in hexane. The solid was collected by filtration and purified by washing excessively with hot $CCL_4$. This wash removeddiscoloration and many of the by-products, but it was not sufficiently effective at removing the residual Pd (II) catalyst from the monomer. The monomer was further purified by chromatography over neutral alumina using tetrahydrofuran as an eluent. The resulting monomer was isolated (32.0 g, 58 percent yield) as a light yellow solid with an m.p. of 172° C. to 174° C. with properties:

$^1H$ NMR (400 MHz, $CDCl_3$): d 7.30–7.40 (12H, br, m), 7.52–7.62 (12H, br, m), 7.82 (2H).

$^{13}C$ NMR (100 MHz, $CDCl_3$): d 88.23 (—C$\underline{C}$Ph, 4C), 93.94 (—$\underline{C}$CPh, 2C) 94.66 (—$\underline{C}$CPh, 2C), 123.5 (4C), 125.26 (2C), 126.49 (4C), 128.5 (m, 12C), 130.16 (2C), 131.76 (8C), 132.38 (2C), 139.19 (2C).

FTIR(cm$^{-1}$): 485.9 (0.17), 503.8 (0.15), 527.9 (0.23), 623.7 (0.05), 687.7 (0.70), 752.8 (1.00), 822.7 (0.38), 886.1 (0.11), 911.5 (0.12), 1022.6 (0.08), 1067.0 (0.12), 1273.9 (0.04), 1384.9 (0.10), 1439.9 (0.18), 1492.44 (0.49), 1534.2 (0.06), 1592.0 (0.19), 2967.2 (0.04), 3028.9 (0.07), 3050.2 (0.08).

Mass Spec, m/e (%): 80 (4), 183 (3.5), 236 (6.2), 237 (9.1), 238 (3.4), 261 (6.8), 262 (8.0), 268 (6.2), 269 (6.0), 274 (22.1), 275 (21.2), 276 (20.0), 277 (21.0), 472 (3.6), 474 (8.8), 476 (4.7), 554 (100), 555 (46.5), 556 (10.6).

Failure to remove the catalyst resulted in a monomer product that underwent premature and excessively rapid polymerization upon heating to the melting point.

EXAMPLE 3

3,3',4,4'-Tetra(phenylethynyl)diphenyl ether 3,3'-Dibromo-4,4-Dihydroxydiphenyl ether To a 2-L, 5-necked Morton flask fitted with a mechanical stirrer, a thermocouple, and a dropping addition funnel was added 1-L of CH$_2$Cl$_2$, 20 mL of HOAc, 100 g of 4,4-dihydroxydiphenyl ether, and 0.74 grams of iron powder. This mixture was stirred and cooled to 10° C. under a nitrogen atmosphere. 170 G of liquid bromine was slowly added to the reaction mixture over a period of 2 hours and 15 minutes with vigorous stirring of the mixture. The temperature of the reaction mixture was maintained between 7° C. and 10° C. during this addition. When completed, the temperature was raised to 18° C. and held at that temperature with stirring for 18 hours. The resulting mixture was then washed with 2-L of water followed by 500 mL of saturated sodium bicarbonate solution. The remaining organic solution was filtered to remove suspended solids, and the filtrate evaporated to remove the solvent. The solid residue was washed with water to remove residual HOAC and dried under vacuum, then washed with hexane to remove colored by-products. The solid residue was dried under vacuum to provide 155 g of a white crystalline solid product (86.3 percent yield) having, as indicated by GC a purity of 97.1 percent with a melting point of 101° C. to 102.5° C. The product had these characteristics:

GC/MS, m/e (%): 51 (16.0), 53 (27.0), 63 (30.0), 79 (16.5), 144 (7.4), 199 (7.3), 200 (13.0), 359 (42.2), 360 (100), 362 (46.9).

FTIR (cm-1): 799 (0.29), 859 (0.30), 880 (0.09), 922 (0.37), 1031 (0.13), 1184 (0.81), 1259 (0.40), 1331 (0.35), 1475 (1.00), 1577 (0.10), 1600 (0.13), 3395 (0.35), 3421 (0.38).

3,3'Dibromo-4,4'-bis(trifluoromethanesulfonato) diphenyl ether

Into a 2-L, 5-necked Morton flask equipped with a mechanical stirrer, a thermocouple, and a dropping addition funnel with a nitrogen pad attached, was added 1-L of CH$_2$Cl$_2$ and 155 g of 3,3'-dibromo-4,4'-dihydroxydiphenyl ether. The solution was cooled to 10° C. Triethylamine (97.75 g) was added dropwise, from the dropping funnel, over a period of 30 minutes, with the reactor temperature being maintained at 10° C. during addition. The dropping funnel was cleaned and dried. Trifluoromethanesulfonic acid anhydride (250.8 g) was added at a rate that maintained a reaction temperature between 10° C. to 20° C. Upon complete addition, the reaction mixture was stirred at 15° C. for 3 hours and then washed with two 500 mL portions of water, followed by one 250 mL portion of saturated sodium bicarbonate solution. The CH$_2$Cl$_2$ was evaporated and the residue was dissolved in acetonitrile to form a 50 percent solution. This solution of the crude reaction mixture was extracted five times with 250 mL portions of hexane. The extracts were combined, and the solvent reduced to crystallize the product, which was then filtered and isolated as a white crystalline powder (165 grams, 98.6 percent pure, 65 percent yield) with a melting point of 46° C. to 47° C.

GC/MS, m/e (%): 63 (41.0), 69 (59.1), 142 (6.8), 144 (5.5), 198 (6.3), 356 (10.4), 357 (7.6), 490 (11.0), 491 (35.5), 492 (100), 493 (46.6), 494 (7.1), 621 (1.5), 623 (2.7), 625 (1.5).

FTIR (cm-1): 823 (0.12), 878 (0.75), 1036 (0.12), 1137 (0.68), 1162 (0.72), 1212 (1.00), 1296 (0.17), 1426 (0.81), 1474 (0.82), 583 (0.21).

3,3',4,4'-Tetra(phenylethynyl)diphenyl ether

A solution of 50 g 3,3'-dibromo-4,4'-bis (trifluoromethane-sulfonato)diphenyl ether (0.080 mole) in triethylamine (180 mL) and DMF (180) in a 1-L, 5-necked round-bottomed flask was deoxygenated thoroughly with nitrogen for 30 minutes. To the deoxygenated solution was added 3.0 g of dichloro bis(triphenylphosphine) palladium (II). The temperature of the flask was raised to 75° C. A dropping addition funnel was placed on the flask and 49 g of phenylacetylene, deoxygenated for 15 minutes, was added at a rate to maintain a reaction temperature of 80° C. to 95° C. When phenylacetylene addition was complete, the reaction mixture was held at a temperature of 90° C. to 91° C. for two hours with a continuous purge of nitrogen. An additional 2.5 g of phenylacetylene was then added to the reaction mixture and the mixture heated at 90° C. to 91° C. for an additional 45 minutes. After cooling the mixture to room temperature, 350 mL of CH$_2$Cl$_2$ was added and the mixture washed with three 500 mL portions of 10 percent HCl solution, followed by one 500 mL wash with deionized water. The organic solution was evaporated to remove the solvent and the residue was purified using a liquid chromatography having silica gel as a stationary phase and CCl$_4$ as a mobile phase. A total of 45 g (0.0789 mole) of monomer was isolated by this method with a 98 percent yield. Analysis of this monomer by LC/MS indicated a purity of greater than 98.5 percent. This monomer had an m.p. of 107° C. to 108° C. and the following characteristics:

$^1$H NMR (400 MHz, CDCl$_3$): d 6.96–6.98 (2H, dd), 7.17 (2H, d), 7.30 (12H, m), 7.51–7.53 (8H, m).

$^{13}$C NMR (100 MHz, CDCl$_3$): d 87.63 (1C, —CC—), 87.74 (1C, —CC—), 93.23 (1C, —CC—), 94.41 (1C, —CC—) 119.23 (1C), 121.44 (1C), 121.77 (1C), 122.90 (1C), 123.28 (1C), 127.59 (1C), 128.37 (4C), 128.64 (1C), 131.57 (2C), 131.72 (2C), 133.50, (1C), 156.11 (1C).

FTIR (cm-1): 689 (0.77), 784 (0.59), 824 (0.39), 878 (0.34), 913 (0.27), 970 (0.42), 1025 (0.25), 1071 (0.28), 1084 (0.28), 1139 (0.33) 1214 (1.00), 1252 (0.52), 1323 (0.47), 1378 (0.17), 1415 (0.41), 1443 (0.38), 1471 (0.64), 1495 (0.82), 1553 (0.40), 1588 (0.65), 2210 (0.16), 3058 (0.27).

Mass Spec m/e (%): 263 (10.1), 265 (10.7), 274 (6.9), 275 (5.65), 276 (2.33), 463 (5.71), 464 (4.33), 539 (4.17), 570 (100), 571 (36.3), 572 (9.51).

EXAMPLE 4

9,9-Bis((3,3',4,4'-tetraphenylethynyl)phenyl)fluorene 9,9-Bis((3,3'-dibromo-4-4'-dihydroxy)phenyl) fluorene To a 2-L 5-necked Morton flask essentially the same as used in Example 3 was added 700 mL of CH$_2$Cl$_2$, 50 mL of HOAc, 104 g of 9,9-bis(4-hydroxyphenyl)fluorene, and 1.0 g of iron powder. This mixture was stirred and cooled to 10° C. under a nitrogen atmosphere. While vigorously stirring the reaction mixture, 99 g of liquid bromine was added, from the dropping funnel, to the reaction mixture over a 1 hour and 45 minute period. The reaction temperature was maintained between 8° C. and 10° C. during the bromine addition. Upon complete addition, the reaction temperature is raised to 22° C. and held at that temperature with stirring for 18 hours. The resulting mixture is then washed with 1.5 L of water followed by 500 mL of saturated sodium bicarbonate solution. The remaining organic solution was evaporated to remove the solvent. The solid residue was dissolved in hot hexane which had been saturated with acetonitrile. Upon cooling, a second liquid phase separated to the bottom of the vessel. This second phase contained most of the colored impurities from this reaction and was removed as a means to purify the product. The solvent was removed under vacuum and the remaining solid residue was dried under vacuum to yield 115 g of a white crystalline solid product which corresponds to a yield of 77 percent. This product has an m.p. of 119° C. to 120° C. and the following characteristics:

GC/MS, m/e (%): 63 (16.9), 226 (17.8), 335 (13.7), 427 (9.6), 428 (27.8), 429 (22.3), 430 (15.4), 507 (6.6), 508 (33.3), 509 (100), 510 (36.8), 511 (8.2).

FTIR (cm–1): 743 (0.36), 782 (0.30), 844 (0.21), 932 (0.78), 1017 (0.20), 1096 (0.79), 1129 (0.76), 1167 (0.77), 1199 (1.00), 1272 (0.11), 1326 (0.52), 1447 (0.17), 1503 (0.49), 3065 (0.06).

9,9-Bis((3,3'-dibromo-4-4'-di(trifluoromethanesulfonato))phenyl)fluorene

Into a 2-L 5-necked Morton flask as used above was added 500 mL C $CH_2Cl_2$ and 111.75 g of 9,9-bis((3,3'-dibromo-4-4'-dihydroxy)phenyl)fluorene. The solution was cooled to 10° C. Triethylamine (97.75 g) was added, using the dropping funnel, over a period of 30 minutes while maintaining the reactor temperature at 10° C. Using a cleaned dropping funnel, 250.8 g of trifluoromethanesulfonic acid anhydride was added at a rate that maintained a reaction temperature of 10° C. to 20° C. Upon completion of the addition of trifluoromethanesulfonic anhydride, the reaction mixture was stirred at 15° C. for 3 hours. The reaction solution was then washed with two 500 mL portions of water followed by one 250 mL portion of saturated sodium bicarbonate solution. The $CH_2Cl_2$ was evaporated and the residue dissolved in acetonitrile to form a 50 percent solution. This solution of the crude reaction mixture was extracted with 250 mL portions of hexane. The extracts were combined, and solvent was reduced to crystallize a white powder product. When filtered, it weighed 165 g, and was 98.6 percent pure. This corresponds to a 65 percent yield. The product has an m.p. of 46° C. to 47° C. and the following characteristics:

FTIR (cm–1): 738 (0.39), 786 (0.16), 826 (0.15), 880 (0.50), 1037 (0.29), 1137 (0.68), 1214 (1.00), 1428 (0.74), 1479 (0.42), 1579 (0.10), 3039 (0.07), 3068 (0.09).

LC/MS, m/e (%): 143 (13.2), 145 (9.8), 224 (12.5), 226 (64.4), 227 (21.0), 263 (23.5), 276 (12.0), 277 (7.9), 287 (25.6), 288 (11.1), 289 (86.5), 290 (39.0), 291 (7.9), 317 (16.5), 318 (41.1), 334 (11.4), 345 (14.3), 346 (27.0), 347 (7.07), 369 (11.2), 397 (45.1), 398 (10.5), 399 (37.1), 400 (10.3), 424 (11.20), 425 (46.2), 426 (21.1), 427 (50.1), 428 (10.6), 637 (43.8), 639 (100), 641 (40.4), 770 (25.8), 772 (52.8), 774 (26.0)

9,9-Bis(3,3',4,4'-tetraphenylethynyl)phenyl)fluorene

Fifty g of 9,9-Bis((3,3'-dibromo-4-4'-di(trifluoromethanesulfonato))phenyl)fluorene was placed in a 1-L, 5-necked round bottomed flask equipped with a mechanical stirrer, a dropping addition funnel, a gas dispersion tube and a thermocouple. To the flask is added 150 g triethylamine and 180 mL N,N-dimethylformamide. This mixture was stirred and heated to 45° C. while nitrogen gas is introduced under liquid level into the flask through the gas dispersion tube. To the deoxygenated solution was added 3.0 g of dichloro bis(triphenylphosphine) palladium (II). The reaction mixture was heated to 70° C. and 33.0 g of deoxygenated phenylacetylene was added to the flask over 30 minutes. This phenylacetylene addition was at a controlled rate to maintain the temperature of the reaction mixture at 90° C. After complete addition, the reaction mixture was maintained at 90° C. for 2 hours and 45 minutes at which time an additional 4.7 g of phenylacetylene was added as a single aliquot and the reaction maintained at 90° C. for additional 45 minutes. The solution was then cooled and diluted with 400 mL of $CH_2Cl_2$ and washed with 2-L of 10 percent HCl solution. After evaporation, the residue was dissolved in $CCl_4$ and purified by column chromatography on silica gel using $CCl_4$ $CH_2Cl_2$ as an eluent to provide 32.5 g (69.6 percent yield) of monomer with 98.5 percent purity having the characteristics:

$^1$H NMR (400 MHz, $CDCl_3$): d 7.75–7.81 (4H, dd), 7.52–7.54 (12H, m), 7.38–7.44 (12H, m), 7.27–7.30 (12H, m), 7.13–7.16 (4H, dd).

$^{13}$C NMR (100 MHz, $CDCl_3$): d 64.90 (1C, spiro), 88.08 (1C, —CC—), 88.36 (1C, —CC—), 93.72 (1C, —CC—), 93.88 (1C, —CC—), 120.45, 123.07, 123.24, 124.57, 125.89, 126.04, 127.89, 128.04, 128.11, 128.28, 128.31, 128.37, 128.42, 131.01, 131.60, 131.65, 131.87, 140.16, 145.53, 149.52.

FTIR (cm–1): 662 (0.12), 688 (0.63), 737 (0.63), 754 (1.00), 823 (0.24), 913 (0.09), 1027 (0.11), 1067 (0.11), 1090 (0.09), 1140 (0.07), 1160 (0.08), 1213 (0.07), 1278 (0.07), 1401 (0.13), 1443 (0.35), 1495 (0.61), 1593 (0.22), 2210 (0.07), 3031 (0.14), 3055 (0.16).

LC/MS, m/e (%): 305 (8.2), 311 (8.3), 312 (9.7), 318 (8.3), 319 (12.1), 363 (16.3), 437 (13.4), 439 (11.1), 441 (20.7), 638 (8.2), 639 (14.8), 640 (12.9), 641 (13.6), 718 (100), 719 (22.4), 720 (12.5).

EXAMPLE 5

Solution Oligomerization, Spin-casting and Curing Thin Films of 2,2-bis(3,4-di(phenylethynyl)phenyl)-1,1,1,3,3,3-hexafluoropropane onto Silicon Substrates To a 25 mL Schlenk tube equipped with nitrogen purge and magnetic stirrer was added 1.0 g (1.42 millimole) of 2,2-bis(3,4-di(phenylethynyl)phenyl)-1,1,1,3,3,3-hexafluoropropane made in Example 1, and 1.0 g of 1,3,5-triisopropylbenzene. The flask was thoroughly purged with dry nitrogen and heated in an oil bath to 210° C. for 12 hours while continuously stirring the solution. The resulting oligomeric product exhibited a relative GPC $M_w$ of 1000, an $M_w/M_n$ of 1.5 and $M_z$ of 2300 (against a standard of polystyrene in THF), and remained completely soluble at 50 weight percent in triisopropylbenzene at room temperature.

The experiment was repeated using the same monomer, but using the solvents and conditions set forth in Table I to give oligomeric products having the properties shown in the same Table I.

TABLE I

| Reaction | Reaction Solvent | Time at 210° C. | $M_w$ | $M_n$ | $M_w/M_n$ |
|---|---|---|---|---|---|
| 1 | tri-i-propylbenzene | 20 h | 2910 | 1078 | 2.7 |
| 2 | tri-i-propylbenzene | 32 h | 6350 | 1411 | 4.5 |
| 3 | tri-i-propylbenzene | 46 h | 24,400 | 2259 | 10.8 |
| 4 | diphenyl ether | 11.5 | 3014 | 1190 | 2.5 |
| 5 | diphenyl ether | 16.5 h | 5085 | 1476 | 3.5 |
| 6 | diphenyl ether | 20.5 h | 13,89 | 1994 | 7.0 |
| 7 | Dodecane | 15 h | 7844 | 1180 | 6.6 |
| 8 | Di-t-butyl benzene | 12 h | 2788 | 1054 | 2.7 |
| 9 | Di-t-butyl benzene | 18.25 | 5881 | 1376 | 4.3 |

Each of the resulting oligomeric products was spin-cast from solution by pouring the solution directly onto a silicon substrate and spinning at a rate of from 700 to 1000 rpm sufficient to give a 1 μm continuous coating or at 400 rpm to give a 4 μm continuous coating after cure. The coated silicon substrates are cured by heating from 30° C. to 125° C. at 30° C./minute and holding isothermally for 60 minutes, then heating at 30° C./minute to 250° C. and holding isothermally for 60 minutes, and finally heating at 30° C./min to 350° C. and holding isothermally for 60 minute. The coated substrates were allowed to cool slowly to room temperature over 14 hours. To a varying degree, each of the resulting coatings adhered to the silicon and remained uniform without delamination or cracking.

EXAMPLE 6

Bulk Oligomerization of Bis(ortho-diacetylene) Monomers

Each of the bis(ortho-diacetylene) monomers prepared in Examples 1–4 was purified to greater than 99 percent purity by LC by flash chromatography on silica gel using $CCl_4$/cyclohexane (70/30). The monomer was dried overnight at 80° C. to 100° C. under vacuum and stored under nitrogen at room temperature.

To a clean, dry, and nitrogen-filled 25 mL Schlenck flask equipped with a stopcock top for sampling via syringe, nitrogen inlet side-arm, and mechanical stirrer was added 1.5 g of the purified bis(ortho-diacetylene) monomer prepared in Example 1. The flask was placed in a stirred oil bath which had been preheated to 210° C. and a nitrogen purge was decreased to a slight positive pressure. Within 60 seconds, the light yellow transparent melt turned darker yellow, then orange, and eventually dark red to essentially black within 1 hour. During the polymerization, the ability of the oligomeric product to form a coating was determined using a 30 percent mesitylene solution of the oligomer and applying the solution on a silicon wafer or glass slide and removing the excess solvent by centrifugal force to form a film. The experiment was repeated under the variety of conditions as outlined in Table II using the different monomers and reaction times and temperatures specified in the table. The resulting molecular weights of each of these trials is reported in Table II.

TABLE II

| Experiment No. | Monomer of Example No. | Time/Temperature | $M_w$ | $M_n$ | $M_w/M_n$ |
|---|---|---|---|---|---|
| 1 | 1 | 0.5 h/210° C. | 970 | 693 | 1.4 |
| 2 | 1 | 1.6 h/210° C. | 1840 | 836 | 2.2 |
| 3 | 1 | 3.25 h/210° C. | 4570 | 1088 | 4.2 |
| 4 | 1 | 4.42 h/210° C. | 10600 | 1413 | 7.5 |
| 5 | 2 | 4 h/200° C. | 1915 | 709 | 2.7 |

TABLE II-continued

| Experiment No. | Monomer of Example No. | Time/Temperature | $M_w$ | $M_n$ | $M_w/M_n$ |
|---|---|---|---|---|---|
| 6 | 2 | 6.75 h/200° C. | 3732 | 829 | 4.5 |
| 7 | 2 | 9.42 h/200° C. | 7492 | 1041 | 7.2 |
| 8 | 3 | 2.17 h/210° C. | 1191 | 657 | 1.8 |
| 9 | 3 | 4 h/210° C. | 2086 | 788 | 2.7 |
| 10 | 3 | 6 h/210° C. | 4249 | 991 | 4.3 |
| 11 | 4 | 4 h/210° C. | 1448 | 788 | 1.8 |
| 12 | 4 | 6 h/210° C. | 2176 | 9559 | 2.3 |
| 13 | 4 | 7.5 h/210° C. | 3083 | 1177 | 2.6 |

After the desired molecular weight was obtained, each of the mixtures set forth in Table II was allowed to cool to room temperature under nitrogen and then dissolved to form an organic liquid solution filtered, spin-coated on a silicon substrate to a 1 μm thickness, and finally cured thermally under nitrogen giving defect-free or substantially defect-free films.

EXAMPLE 7

Formulation and Application of Oligomer Solutions

Each of the bis(ortho-diacetylene) monomers prepared in Examples 1–4 was purified using the techniques of Example 6. A sample of each of the purified monomers was oligomerized to the molecular weights shown in Table III using the techniques employed in either Example 5 or 6.

The oligomeric products were then formed as a coating on a silicon wafer by applying a solution of the oligomer (the solvent and concentration being recorded in Table III) on a silicon wafer and removing the excess solvent by centrifugal force, followed by exposure to an elevated temperature of 100° C. to form a film. The resulting coating is then cured. This procedure was repeated using the different monomers and solvent systems specified in Table III.

TABLE III

| Monomer of Ex. No. | Coating Soln. % Solids | Solvent | $M_w$ | $M_n$ | $M_w/M_n$ |
|---|---|---|---|---|---|
| 1 | 50 | tri-i-propylbenzene | 6521 | 1475 | 4.4 |
| 1 | 50 | tri-i-propylbenzene | 4867 | 1508 | 3.2 |
| 1 | 30 | 57% mesitylene 43% diphenyl ether | 5085 | 1476 | 3.5 |
| 1 | 30 | 57% mesitylene 43% dodecane | 7844 | 1184 | 6.6 |
| 1 | 30 | 57% mesitylene 43% di-t-butylbenzene | 5881 | 1376 | 4.3 |
| 1 | 40 | mesitylene | 5911 | 1217 | 4.9 |
| 2 | 28 | mesitylene | 9000 | 1096 | 8.4 |
| 2 | 25 | mesitylene | 9245 | 1065 | 8.7 |
| 2 | 25 | 77.3% mesitylene 22.7% diphenyl ether | 7500 | 1042 | 7.2 |
| 2 | 25 | mesitylene | 7500 | 1042 | 7.2 |
| 2 | 35 | cyclopentanone | 8900 | 1099 | 8.1 |
| 3 | 30 | mesitylene | 4300 | 1000 | 4.3 |
| 3 | 40 | mesitylene | 5500 | 1146 | 4.8 |
| 3 | 30 | mesitylene | 10000 | 1000 | 10 |
| 4 | 35 | mesitylene | 3100 | 1192 | 2.6 |
| 4 | 35 | mesitylene | 3200 | 1143 | 2.8 |

Each of the oligomeric materials was easily applied as a coating from solution and, when cured, adhered to the silicon substrate as a defect-free or substantially defect-free film.

EXAMPLE 8

Polymerization of 2,2-bis(3',4'-bis(phenylethynyl)phenyl)-1,1,1,3,3,3-hexafluoropropane (1)

A 28 g sample of 2,2-bis(3',4'-bis(phenylethynyl)phenyl)-1,1,1,3,3,3-hexafluoropropane was heated in an aluminum pan under an inert atmosphere at a temperature of 200° C. to 250° C. for 8 hours giving a hard, glassy, black film in an essentially quantitative yield. The film was intractable and insoluble in common organic solvents and had the following FTIR properties:

FTIR (transmission diamond cell) cm-1: 3059, 3026 (ArH), 1598 (Ar), 1493 (Ar), 1443 (w), 1253 (st, CF), 1206 (st, CF), 1135 (w, sh), 965 (w), 755 (w) cm-1.

A differential scanning calorimetry (DSC) analysis (at 10° C./minute) of the neat monomer (6.73 mg) gave a peak melting endotherm at 163° C. (DH=-62 J/g), an onset of polymerization exotherm at 200° C., peak exotherm at 314° C., and end of exotherm at 380° C., respectively with a ΔH of 583 Joules per gram. Subsequent DSC scans resulted in no detectable thermal transitions. In situ polymerization and thermal stability evaluation by TGA were conducted by heating the neat monomer from room temperature to 200° C. at 200° C./minute, equilibrating at 200° C. for 5 to 10 minutes and then heating at 20° C./minute to 300° C., followed by an isothermal soak at 300° C. for 3 hours. During this cure schedule, no detectable weight loss occurred. Thermal stability was then calculated by increasing the temperature from 300° C. to 450° C. at 10° C./min and holding isothermally at 450° C. for 10 hours. The thermal stability is calculated by measuring the rate of weight loss over the last 9 hours which gives −0.60 percent weight loss per hour. The polymer samples are then heated to 900° C. at 10° C./min and held for 4 hours to assess the char yield calculated by the weight loss after baking at 450° C. for 10 hours until the 4 hour bake at 900° C. is complete.

EXAMPLE 9

Thermal polymerization of bis(ortho-diacetylene) Monomers and Thermal Stability of the Resulting Polymers The monomers of Examples 1–4 were thermally polymerized in a DSC pan according to the procedure set forth in Example 8. The results of each of these DSC analyses appear in Table VI.

The resulting polymers demonstrated the following thermal stabilities as measured by TGA according to the method described in Example 8. The results are tabulated in Table V.

TABLE V

| Polymer from Monomer # | Temp. (° C.) | Weight Loss (percent/hour) at 450° C. tor 10 h | Char yield at 900° C. | Weight Loss (percent/hour) at 900° C. for 3 h |
|---|---|---|---|---|
| 1 | 450 | 1.5 | 88% | <0.1% |
| 2 | 450 | 0.5 | 98% | <0.1% |
| 3 | 450 | 1.0 | 90% | <0.1% |
| 4 | 450 | 1.2 | 93% | <0.1% |

The rate of thermal degradation was measured by the weight loss or the percent weight loss per hour at 450° C.; with each of the polymers exhibiting very good thermal stability, with the monomer of Example 2 being the most superior. The organic char yield was one measure of the polymer's performance at ultra-high temperature (900° C.), with the higher percentages being desired.

What is claimed is:

1. A compound having the structure:

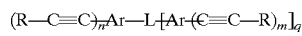

wherein each Ar is an aromatic group or inertly-substituted aromatic group and each Ar comprises at least one aromatic ring; each R is independently hydrogen, an alkyl, aryl or inertly-substituted alkyl or aryl group; L is a covalent bond, an alkyl group of 1 to 20 carbon atoms, biphenyl, phenyl, naphthyl, a fluorene, a polymeric chain, oxygen, sulfur, nitrogen, an inertly-substituted amine, phosphorus, or an inertly-substituted phosphine, provided that the groups Ar and L taken together do not form a fused ring structure; n and m are integers of at least 2; and q is an integer of at least 1, and wherein at least two of the ethynylic groups on one of the aromatic rings are ortho to one another, wherein the inertly-substituted groups are characterized by having one or more substituents that are inert to subsequent polymerization of the compound.

2. The compound of claim 1 wherein each Ar independently has from 6 to 50 carbon atoms.

3. The compounds of claim 2 wherein each R is independently hydrogen or an alkyl, aryl or inertly-substituted alkyl or aryl group having from 1 to 20 carbon atoms.

4. The compound of claim 2 wherein each Ar is independently a phenyl, naphthyl, biphenyl, 9,9-diphenyl fluorene, diphenyl ether, diphenyl sulfide, anthracene, phenanthrene, anthraquinone, triphenyl phosphine, triphenyl phosphine oxide group or an inertly-substituted phenyl, naphthyl, biphenyl, 9,9-diphenyl fluorene, diphenyl ether, diphenyl sulfide, anthracene, phenanthrene, anthraquinone, triphenyl phosphine, or triphenyl phosphine oxide group.

TABLE VI

| Monomer of Example no. | Melt Temperature (° C.) | DSC exotherm onset T ° C. | DSC exotherm max T ° C. | DSC exotherm end T ° C. | DSC exotherm ΔH (J/g) |
|---|---|---|---|---|---|
| 1 | 163 | 210 | 314 | 375 | −583 |
| 2 | 173 | 200 | 300 | 440 | −789 |
| 3 | 108 | 205 | 303 | 430 | −693 |
| 4 | 105 | 210 | 310 | 360 | −413 |

5. The compound of claim 2 wherein each R is independently phenyl, naphthyl, biphenyl, 9,9-diphenyl fluorene, diphenyl ether, diphenyl sulfide, anthracene, phenanthrene, anthraquinone, triphenyl phosphine, or triphenyl phosphine oxide groups.

6. The compound of claim 2 wherein at least one Ar is an aromatic group substituted with an alkyl, halogen, perfluorocarbon, or a combination thereof, and at least one R group is an alkyl or aryl group substituted with an aryl, halogen, perfluorocarbon or a combination thereof.

7. The compound of claim 2 wherein at least one Ar is an aromatic group substituted with fluorine, chlorine or bromine or at least one R group is substituted with fluorine, chlorine or bromine.

8. The compound of claim 1 wherein L is a covalent bond, an unsubstituted or inertly-substituted alkyl group, sulfur, phosphorous, or oxygen.

9. The compound of claim 8 wherein L is a covalent bond, 2,2-propane, sulfur, oxygen, phosphorus, or 1,1,1,3,3,3-hexafluoro-2,2-propane.

10. The compound of claim 8 wherein L is an unsubstituted or inertly-substituted alkyl group of from 1 to 20 carbon atoms.

11. The compound of claim 10 wherein L has from 3 to 6 carbon atoms.

12. The compound of claim 1 wherein L is selected from biphenyl, phenyl, or naphthyl.

13. The compound of claim 1 wherein each R is independently hydrogen or is unsubtituted or inertly-substituted phenyl.

14. The compound of claim 13 wherein each R is independently phenyl substituted with one or more fluorine atoms or fluoroalkyl groups of from 1 to 6 carbon atoms.

15. The compound of claim 1 wherein each Ar has two ethynylic groups that are positioned ortho to one another on the aromatic ring.

16. A compound having the structure:

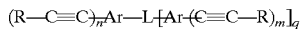

wherein each Ar is an aromatic group and each Ar comprises at least one aromatic ring; each R is independently hydrogen, an alkyl, aryl group; L is a covalent bond, an alkyl group of 1 to 20 carbon atoms, biphenyl, phenyl, or naphthyl, a fluorene, a polymeric chain, oxygen, sulfur, nitrogen, a substituted amine, phosphorus, or substituted phosphine, provided that the groups Ar and L taken together do not form a fused ring structure; n and m are integers of at least 2; and q is an integer of at least 1, and wherein at least two of the ethynylic groups on one of the aromatic rings are ortho to one another, wherein each Ar or R, optionally, has one or more substituents selected from alkyl groups, halogens, alkenes, phosphorus, silicon, sulfur, nitrogen, oxygen, —$CF_3$, —$OCH_3$, —$OCF_3$, and —O—Ph.

* * * * *